US011638000B2

(12) United States Patent
Honda

(10) Patent No.: US 11,638,000 B2
(45) Date of Patent: Apr. 25, 2023

(54) MEDICAL OBSERVATION APPARATUS

(71) Applicant: Sony Olympus Medical Solutions Inc., Tokyo (JP)

(72) Inventor: Takeshi Honda, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/525,587

(22) Filed: Jul. 30, 2019

(65) Prior Publication Data

US 2020/0045293 A1  Feb. 6, 2020

(30) Foreign Application Priority Data

Aug. 6, 2018  (JP) .............................. JP2018-147585

(51) Int. Cl.
*H04N 13/183* (2018.01)
*A61B 1/00* (2006.01)
(Continued)

(52) U.S. Cl.
CPC ......... *H04N 13/183* (2018.05); *A61B 1/0005* (2013.01); *A61B 1/000094* (2022.02); *A61B 1/00149* (2013.01); *A61B 1/00193* (2013.01); *A61B 1/0655* (2022.02); *G06T 7/70* (2017.01); *H04N 5/272* (2013.01); *H04N 13/239* (2018.05); *G06T 2207/10068* (2013.01); *G06T 2207/30244* (2013.01)

(58) Field of Classification Search
CPC ............ A61B 1/00006; A61B 1/00009; A61B 1/00011; A61B 1/0005; A61B 1/00105; A61B 1/00149; A61B 1/00186; A61B 1/00193; A61B 1/042; A61B 1/043; A61B 1/045; A61B 1/0638; A61B 1/07; G06T 2207/10068; G06T 2207/30244; G06T 7/70; H04N 13/183; H04N 13/239; H04N 5/272

See application file for complete search history.

(56) References Cited

U.S. PATENT DOCUMENTS

2009/0003671 A1\*  1/2009  Inoue .................. G06T 7/13
382/128
2009/0073257 A1\*  3/2009  Tanaka .................. G06T 17/00
348/45
(Continued)

FOREIGN PATENT DOCUMENTS

EP  2358269 B1 \*  4/2019 ........... A61B 1/0005
JP  2002253480 A  9/2002
(Continued)

*Primary Examiner* — Md N Haque
(74) *Attorney, Agent, or Firm* — Xsensus LLP

(57) ABSTRACT

A medical observation apparatus includes: an imaging device configured to capture an observation target to obtain a captured right eye medical image and a captured left eye medical image; and circuitry configured to: acquire positions of at least two points in the observation target, the positions being determined based on predetermined operation on the observation target; and cause the captured right eye medical image, the captured left eye medical image, and an annotation image, to be displayed on a display screen of a display device, the annotation image indicating a distance between two points at the acquired positions.

18 Claims, 13 Drawing Sheets

(51) Int. Cl.
*H04N 13/239* (2018.01)
*H04N 5/272* (2006.01)
*G06T 7/70* (2017.01)
*A61B 1/06* (2006.01)

(56) References Cited

U.S. PATENT DOCUMENTS

| | | | | |
|---|---|---|---|---|
| 2009/0220133 | A1* | 9/2009 | Sawa | G06T 7/0012 |
| | | | | 382/128 |
| 2009/0306514 | A1* | 12/2009 | Imamura | G01S 7/52074 |
| | | | | 600/458 |
| 2013/0009958 | A1* | 1/2013 | Kitamura | A61B 6/503 |
| | | | | 345/424 |
| 2014/0037177 | A1* | 2/2014 | Endo | G06T 7/33 |
| | | | | 382/131 |
| 2015/0030229 | A1* | 1/2015 | Borsdorf | A61B 6/501 |
| | | | | 382/132 |
| 2015/0085081 | A1* | 3/2015 | Shioda | G02B 21/365 |
| | | | | 348/47 |
| 2016/0165222 | A1* | 6/2016 | Yamaoka | A61B 90/20 |
| | | | | 348/51 |

FOREIGN PATENT DOCUMENTS

| | | |
|---|---|---|
| JP | 2007-521864 A | 8/2007 |
| JP | 2009014711 A | 1/2009 |
| JP | 2009168499 A | 7/2009 |
| JP | 2011145527 A | 7/2011 |
| JP | 2012-75507 A | 4/2012 |
| JP | 2012147857 A | 8/2012 |
| JP | 2013005830 A | 1/2013 |
| JP | 2013137466 A | 7/2013 |
| JP | 2014010098 A | 1/2014 |
| JP | 2014-66788 A | 4/2014 |
| JP | 2014-94246 A | 5/2014 |
| JP | 2015-104447 A | 6/2015 |
| JP | 2015211824 A | 11/2015 |
| JP | 2016131866 A | 7/2016 |
| WO | WO-2014156378 A1 | 10/2014 |

* cited by examiner

MEDICAL OBSERVATION APPARATUS

CROSS-REFERENCE TO RELATED APPLICATION

The present application claims priority to and incorporates by reference the entire contents of Japanese Patent Application No. 2018-147585 filed in Japan on Aug. 6, 2018.

BACKGROUND

The present disclosure relates to a medical observation apparatus.

In recent medical settings, a medical observation apparatus, which enables magnified observation of an observation target, such as a lesion, may be used, for example, for support of a microsurgery, such as a neurosurgical operation, or for an endoscopic surgical operation. Examples of this medical observation apparatus include: a medical observation apparatus including an optical microscope; and a medical observation apparatus including an imaging device that functions as an electronic imaging microscope. Hereinafter, a medical observation apparatus including an optical microscope as mentioned above will be referred to as an "optical medical observation apparatus". Furthermore, hereinafter, a medical observation apparatus including an imaging device as mentioned above may be referred to as an "electronic imaging medical observation apparatus" or simply as a "medical observation apparatus". Moreover, hereinafter, a captured image (a moving image or a static image, the same applying hereinafter) having an observation target captured therein by an imaging device included in a medical observation apparatus will be referred to as a "captured medical image".

Electronic imaging medical observation apparatuses now enable acquisition of image quality equivalent to or better than that by optical medical observation apparatuses because of increase in image quality of imaging devices and increase in image quality of display devices where captured images are displayed. Furthermore, a user who uses an electronic imaging medical observation apparatus (for example, a medical worker, such as a surgical operator or an assistant of the surgical operator, the same applying hereinafter) does not need to look into an eyepiece forming an optical microscope as done in a case where an optical medical observation apparatus is used, and thus position of its imaging device is able to be moved more freely. Therefore, due to an advantage that use of electronic imaging medical observation apparatuses enables microsurgeries and the like to be supported more flexibly, use of electronic imaging medical observation apparatuses in medical settings has been promoted.

A technique related to a graphical user interface (GUI) related to medical images has also been developed. A technique described in Japanese Translation of PCT International Application, Publication No. 2007-521864 cited below is an example of this technique.

SUMMARY

Display of a GUI object, such as a diameter measuring object, on a captured medical image, for example, is realized by use of the technique described in Japanese Translation of PCT International Application, Publication No. 2007-521864. For example, use of the technique described in Japanese Translation of PCT International Application, Publication No. 2007-521864 realizes display of the diameter measuring object for a contour included in the captured medical image. When the diameter measuring object is displayed for the contour included in the captured medical image as described above, a person looking at the captured medical image displayed on a display screen is able to visually recognize the diameter of the contour.

However, when the technique described in Japanese Translation of PCT International Application, Publication No. 2007-521864 is used, for example, unless the diameter measuring object is displayed for the contour included in the captured medical image by manipulation of the GUI, the person looking at the captured medical image is unable to recognize the diameter of the contour. The manipulation of the GUI is considered to be manipulation having low relevance to "medical intervention performed by a medical worker, such as a surgical operator (a surgeon) or an assistant, by use of a medical observation apparatus". Therefore, when the technique described in Japanese Translation of PCT International Application, Publication No. 2007-521864 is used, for example, medical intervention may be interrupted by the manipulation of the GUI, and the interruption of the medical intervention may lead to reduction in convenience for the medical worker using the medical observation apparatus. Hereinafter, a person, such as a surgical operator or an assistant, who uses a medical observation apparatus will be referred to as a "user of the medical observation apparatus", or simply as a "user".

A medical observation apparatus according to one aspect of the present disclosure includes: an imaging device configured to capture an observation target to obtain a captured right eye medical image and a captured left eye medical image; and circuitry configured to: acquire positions of at least two points in the observation target, the positions being determined based on predetermined operation on the observation target; and cause the captured right eye medical image, the captured left eye medical image, and an annotation image, to be displayed on a display screen of a display device, the annotation image indicating a distance between two points at the acquired positions.

DETAILED DESCRIPTION

Hereinafter, preferred embodiments of the present disclosure will be described in detail while reference is made to the appended drawings. Redundant explanation of any components having substantially the same functional configuration will be omitted by assignment of the same reference sign to these components throughout the specification and drawings.

Furthermore, hereinafter, the description will be made in the following order.
1. Medical Observation System According to Embodiment and Display Control Method According to Embodiment
 [1] Configuration of Medical Observation System
  [1-1] Medical Observation System According to First Example
  [1-2] Medical Observation System According to Second Example
  [1-3] Functional Configuration of Medical Observation Apparatus
 [2] Display Control Method According to Embodiment
 [2-1] Outline of Display Control Method According to Embodiment
 [2-2] Example of Processing Related to Display Control Method According to Embodiment
 [3] Example of Effects Achieved by Use of Display Control Method According to Embodiment
2. Program According to Embodiment Medical Observation System According to Embodiment and Display Control Method According to Embodiment Hereinafter, an example of a medical observation system according to an embodiment will be described, and a medical observation method according to the embodiment will also be described.

A case where a medical observation apparatus according to the embodiment performs processing related to the display control method according to the embodiment will be described mainly below. In the medical observation system according to the embodiment, an apparatus that is able to perform the processing related to the display control method according to the embodiment is not limited to the medical observation apparatus according to the embodiment. For example, in the medical observation system according to the embodiment, any apparatus, such as a medical controller, may perform the processing related to the display control method according to the embodiment.

Figure 1:
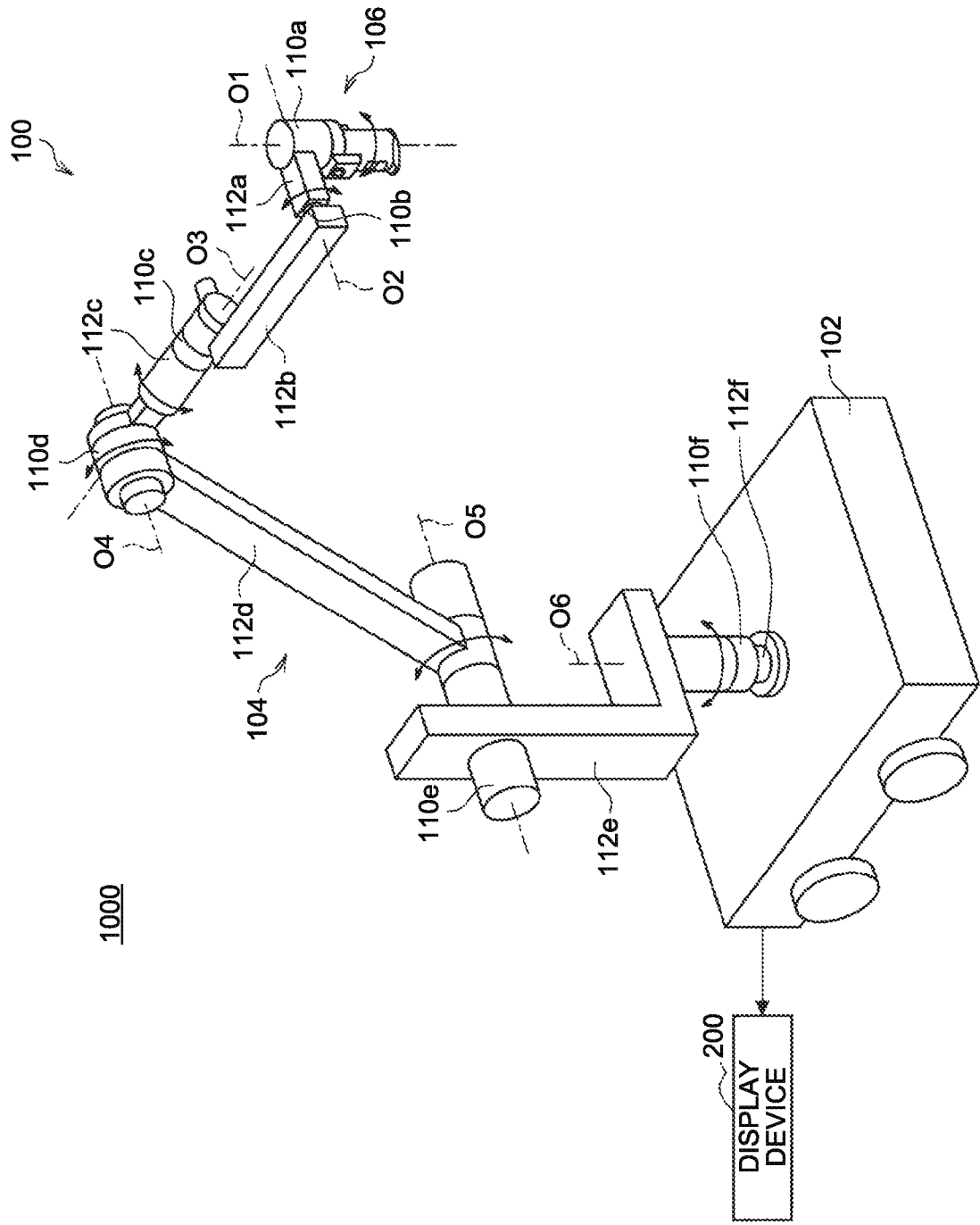
FIG. 1 is an explanatory diagram illustrating a first example of a configuration of a medical observation system according to an embodiment.

[1] Configuration of Medical Observation System
[1-1] Medical Observation System According to First Example FIG. 1 is an explanatory diagram illustrating a first example of a configuration of a medical observation system 1000 according to the embodiment. The medical observation system 1000 illustrated in FIG. 1 has, for example, a medical observation apparatus 100, and a display device 200.

A medical observation system according to the first example is not limited to the example illustrated in FIG. 1.

For example, the medical observation system according to the first example may further have a medical control device (not illustrated in the drawings) that controls various types of operation in the medical observation apparatus 100. As described later, the medical observation system 1000 illustrated in FIG. 1 represents an example where the medical observation apparatus 100 has functions of the medical control device (not illustrated in the drawings) by the medical observation apparatus 100 including a control unit (described later).

Examples of the medical control device (not illustrated in the drawings) include: a "medical controller"; and "a computer, such as a server" Furthermore, the medical control device (not illustrated in the drawings) may be, for example, an integrated circuit (IC) that is able to be incorporated in a device as described above.

Furthermore, the medical observation system according to the first example may be configured to have: plural medical observation apparatuses 100; plural display devices 200; or both plural medical observation apparatuses 100 and plural display devices 200. If the medical observation system has plural medical observation apparatuses 100, the processing related to the display control method described later is performed in each of the medical observation apparatuses 100. Moreover, if the medical observation system according to the first example is configured to have plural medical observation apparatuses 100 and plural display devices 200, the medical observation apparatuses 100 and the display devices 200 may have one-to-one correspondence, or more than one medical observation apparatus 100 may be associated with one display device 200. If more than one medical observation apparatus 100 is associated with one display device 200, which one of captured medical images respectively captured by these medical observation apparatuses 100 is to be displayed on a display screen is changed in the display device 200 by, for example, a switch-over manipulation.

Furthermore, the medical observation system according to the embodiment may further have a navigation device. The navigation device is a medical device for realizing a so-called medical navigation system. For example, the navigation device detects a spatial position of a position detecting probe, and causes an image corresponding to the detected spatial position to be displayed on a display screen of an arbitrary display device. The navigation device is driven by, for example, electric power supplied from an internal power source, such as a battery, which is included in the navigation device, or electric power supplied from an external power source connected to the navigation device.

When the medical navigation system is realized by the navigation device, for example, a medical worker moves the position detecting probe to a position corresponding to a site of surgical operation. In this case, the position corresponding to the site of surgical operation is detected. The navigation device detects a position of a site of surgical operation in a patient by detecting a spatial position of the position detecting probe by any position detecting method, such as an optical position detecting method where infrared light or the like is used, or a magnetic field type position detecting method. For example, a position sensor that detects the spatial position of the position detecting probe may be included in the navigation device, or may be provided at any position outside the navigation device. For example, when a position of a site of surgical operation in a patient is detected, by looking at an image, which is displayed on a display screen and corresponds to a detected spatial position, a medical worker, such as a surgical operator, is able to visually recognize which part of the patient a portion being treated corresponds to.

The navigation device may have a function of transmitting positional information indicating the detected spatial position of the position detecting probe, to an external device, such as the medical observation apparatus 100. The navigation device corresponds to an example of a detecting device that detects a position in an observation target.

Figure 2:
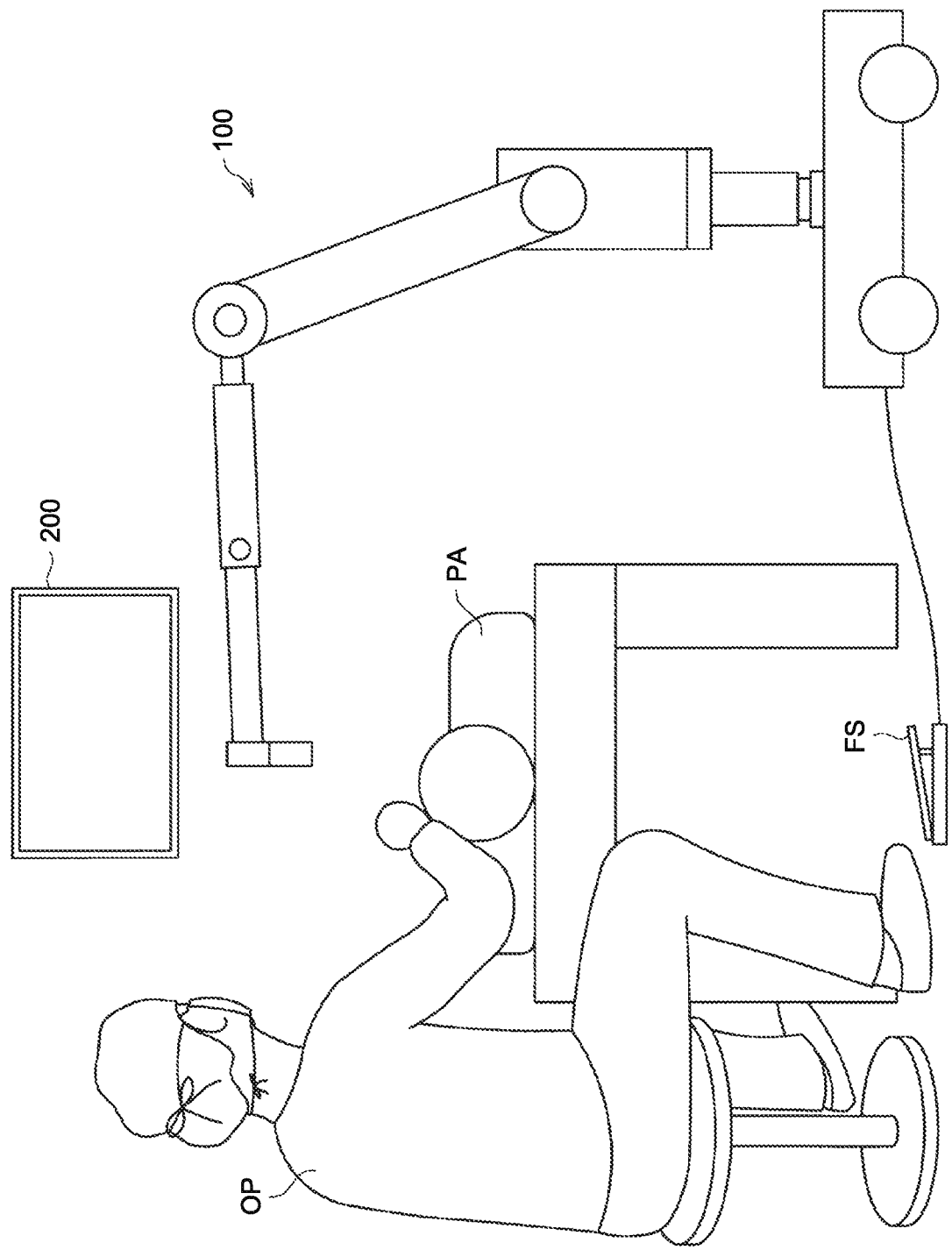
FIG. 2 is an explanatory diagram illustrating an example of a use case where the medical observation system according to the embodiment is used.

FIG. 2 is an explanatory diagram illustrating an example of a use case where the medical observation system 1000 according to the embodiment is used, and illustrates an example of a use case where the medical observation system 1000 according to the first example is used.

An image of a patient PA (a patient to receive medical intervention) who is an observation target is captured by an imaging device (described later) included in the medical observation apparatus 100. A captured image having the patient PA captured therein, the patient PA being a target that receives the medical intervention, corresponds to an example of a captured medical image.

The captured medical image captured in the medical observation apparatus 100 is displayed on the display screen of the display device 200. A surgical operator (OP) (an example of a user of the medical observation apparatus 100) who performs the medical intervention by using the medical observation apparatus 100 performs the medical intervention on the patient PA while looking at the captured medical image being displayed on the display screen of the display device 200.

Furthermore, the surgical operator OP causes an arm (described later), the imaging device (described later), or the like, which is included in the medical observation apparatus 100, to operate and the medical observation apparatus 100 to be brought into a desired state, by manipulating a manipulation device, such as a foot switch FS, which is external to the medical observation apparatus 100, or a manipulation device (described later) included in the medical observation apparatus 100.

Each device forming the medical observation system 1000 according to the first example illustrated in FIG. 1 will be described below.

[1-1-1] Display Device 200

The display device 200 is a display means in the medical observation system 1000 according to the first example, and corresponds to a display device external to the medical observation apparatus 100. The display device 200 displays, for example, various images, such as a captured medical image captured in the medical observation apparatus 100 and an image related to a user interface (UI), on the display screen. Furthermore, the display device 200 may have a configuration enabling 3D display by an arbitrary method. Display in the display device 200 is controlled by, for example, the medical observation apparatus 100 or the medical control device (not illustrated in the drawings).

In the medical observation system 1000, the display device 200 is installed at an arbitrary place, such as a wall surface, a ceiling, or a floor surface, of a surgical operating room, the arbitrary place being visually recognizable by a person, such as a surgical operator, who is involved in a surgical operation in the surgical operating room.

Examples of the display device 200 include a liquid crystal display, an organic electro-luminescence (EL) display, and a cathode ray tube (CRT) display.

The display device 200 is not limited to the example described above. For example, the display device 200 may be any wearable device, such as a head mounted display or an eyewear device, which is used by being worn by the surgical operator or the like on the body.

The display device 200 is driven by, for example, electric power supplied from an internal power source, such as a battery, which is included in the display device 200, or electric power supplied from an external power source connected to the display device 200.

[1-1-2] Medical Observation Apparatus 100

The medical observation apparatus 100 illustrated in FIG. 1 is an example of an electronic imaging medical observation apparatus. When the medical observation apparatus 100 illustrated in FIG. 1 is used in a surgical operation, for example, a surgical operator (an example of a user of the medical observation apparatus 100, the same applying hereinafter) observes a site of surgical operation (a lesion) while referring to a captured medical image captured by the medical observation apparatus 100 and displayed on the display screen of the display device 200, and performs various treatments, such as maneuvers, according to operative surgical procedures, on the site of surgical operation.

As illustrated in FIG. 1, the medical observation apparatus 100 includes, for example, a base 102, an arm 104, and an imaging device 106.

Furthermore, the medical observation apparatus 100 may include, for example: one or more processors (not illustrated in the drawings) each formed of an arithmetic operation circuit, such as a micro processing unit (MPU); a read only memory (ROM, not illustrated in the drawings); a random access memory (RAM, not illustrated in the drawings); a recording medium (not illustrated in the drawings); and a communication device (not illustrated in the drawings), which are all not illustrated in FIG. 1. The medical observation apparatus 100 is driven by, for example, electric power supplied from an internal power source, such as a battery, which is included in the medical observation apparatus 100, or electric power supplied from an external power source connected to the medical observation apparatus 100.

The processor (not illustrated in the drawings) functions as the control unit (described later) in the medical observation apparatus 100. The ROM (not illustrated in the drawings) stores therein a program used by the processor (not illustrated in the drawings) and control data, such as arithmetic operation parameters. The RAM (not illustrated in the drawings) temporarily stores therein the program executed by the processor (not illustrated in the drawings).

The recording medium (not illustrated in the drawings) functions as a storage unit (not illustrated in the drawings) in the medical observation apparatus 100. For example, the recording medium (not illustrated in the drawings) has, stored therein, various data, such as data related to the display control method according to the embodiment, and various applications. Examples of the recording medium (not illustrated in the drawings) include a magnetic recording medium, such as a hard disk, and a non-volatile memory, such as a flash memory. Furthermore, the recording medium (not illustrated in the drawings) may be attachable to and detachable from the medical observation apparatus 100.

The communication device (not illustrated in the drawings) is a communication means included in the medical observation apparatus 100, and plays a role of performing communication wirelessly or wiredly with an external device, such as the display device 200. The communication device (not illustrated in the drawings) may be, for example: an IEEE 802.15.1 port and a transmitting and receiving circuit (wireless communication); an IEEE 802.11 port and a transmitting and receiving circuit (wireless communication); a communication antenna and a radio frequency (RF) circuit (wireless communication); or a local area network (LAN) terminal and a transmitting and receiving circuit (wired communication).

[1-1-2-1] Base 102

The base 102 is a base of the medical observation apparatus 100, has one end of the arm 104 connected thereto, and supports the arm 104 and the imaging device 106.

Furthermore, the base 102 has, for example, wheels provided therein, and the medical observation apparatus 100 contacts a floor surface via the wheels. By the provision of the wheels, the medical observation apparatus 100 is able to easily move on the floor surface by means of the wheels.

[1-1-2-2] Arm 104

The arm 104 is formed of plural links connected to one another via joints.

Furthermore, the arm 104 supports the imaging device 106. The imaging device 106 supported by the arm 104 is three-dimensionally movable, and the position and posture of the imaging device 106 that has been moved are retained by the arm 104.

More specifically, the arm 104 is formed of, for example, plural joints 110a, 110b, 110c, 110d, 110e, and 110f, and plural links 112a, 112b, 112c, 112d, 112e, and 112f that are rotatably connected to one another via the joints 110a, 110b, 110c, 110d, 110e, and 110f. A rotatable range of each of the joints 110a, 110b, 110c, 110d, 110e, and 110f is arbitrarily set in the design phase and manufacturing phase, such that desired movement of the arm 104 is realized.

That is, in the medical observation apparatus 100 illustrated in FIG. 1, six degrees of freedom are realized with respect to movement of the imaging device 106 by means of six rotation axes (a first axis O1, a second axis O2, a third axis O3, a fourth axis O4, a fifth axis O5, and a sixth axis O6) corresponding to the six joints 110a, 110b, 110c, 110d, 110e, and 110f that form the arm 104. More specifically, in the medical observation apparatus 100 illustrated in FIG. 1, movement of six degrees of freedom, which are three degrees of translational freedom and three degrees of rotational freedom, is realized.

The joints 110a, 110b, 110c, 110d, 110e, and 110f each have an actuator (not illustrated in the drawings) provided therein, and the joints 110a, 110b, 110c, 110d, 110e, and 110f respectively rotate about the rotational axes corresponding thereto by drive of the actuators (not illustrated in the drawings). The drive by the actuators (not illustrated in the drawings) is controlled by, for example, the processor that functions as the control unit described later, or the external medical control device (not illustrated in the drawings).

The joints 110a, 110b, 110c, 110d, 110e, and 110f may respectively have, provided therein, angle sensors (not illustrated in the drawings) that are able to detect rotation angles about the six rotation axes respectively. The angle sensors may be any sensors, such as rotary encoders or angular velocity sensors, which are able to obtain the rotation angles about the six rotation axes respectively.

By rotation of the joints 110a, 110b, 110c, 110d, 110e, and 110f respectively about the corresponding rotation axes through the drive of the actuators (not illustrated in the drawings), various types of operation of the arm 104, such as, for example, extension and shortening (folding) of the arm 104, are realized.

The joint 110a has a substantially columnar shape, and supports the imaging device 106 (an upper end portion of the imaging device 106 in FIG. 1) rotatably about the rotation axis (the first axis O1) parallel to a center axis of the imaging device 106, by means of a distal end position (a lower end portion in FIG. 1) of the joint 110a. The medical observation apparatus 100 is formed such that the first axis O1 coincides with the optical axis in the imaging device 106. That is, by rotation of the imaging device 106 about the first axis O1 illustrated in FIG. 1, a captured medical image captured by the imaging device 106 becomes an image where the field of view is changed as if being rotated.

The link 112a is a member that is substantially rod shaped, and supports the joint 110a fixedly. The link 112a is, for example, extended in a direction orthogonal to the first axis O1, and connected to the joint 110b.

The joint 110b has a substantially columnar shape, and supports the link 112a rotatably about the rotation axis (the second axis O2) orthogonal to the first axis O1. Furthermore, the joint 110b has the link 112b fixedly connected thereto.

The link 112b is a member that is substantially rod shaped, and is extended in a direction orthogonal to the second axis O2. Furthermore, each of the joint 110b and joint 110c is connected to the link 112b.

The joint 110c has a substantially columnar shape, and supports the link 112b rotatably about the rotation axis (the third axis O3) orthogonal to each of the first axis O1 and second axis O2. Furthermore, one end of the link 112c is fixedly connected to the joint 110c.

By rotation of a distal end (an end where the imaging device 106 is provided) of the arm 104 about the second axis O2 and third axis O3, the imaging device 106 is able to be moved such that position of the imaging device 106 is changed in a horizontal plane. That is, in the medical observation apparatus 100, control of rotation about the second axis O2 and third axis O3 enables movement of the field of view of a captured medical image in a plane.

The link 112c is a member, which has one end having a substantially columnar shape, and another end that is substantially rod shaped. The joint 110c is fixedly connected to the one end of the link 112c, such that the center axis of the joint 110c coincides with the center axis of the substantially columnar shape. Furthermore, the joint 110d is connected to the other end of the link 112c. The joint 110d has a substantially columnar shape, and supports the link 112c rotatably about the rotation axis (the fourth axis O4) orthogonal to the third axis O3. The joint 110d has the link 112d connected fixedly thereto.

The link 112d is a substantially rod shaped member, and is extended orthogonally to the fourth axis O4. One end of the link 112d is fixedly connected to the joint 110d, so as to abut a side surface of the substantially columnar shape of the joint 110d. Furthermore, the joint 110e is connected to the other end of the link 112d (an end opposite to the end connected to the joint 110d).

The joint 110e has a substantially columnar shape, and supports the other end of the link 112d rotatably about the rotation axis (the fifth axis O5) parallel to the fourth axis O4. Furthermore, the one end of the link 112e is fixedly connected to the joint 110e.

The fourth axis O4 and the fifth axis O5 are rotation axes that allow the imaging device 106 to be moved in a vertical direction. By rotation of the distal end (the end where the imaging device 106 is provided) of the arm 104 about the fourth axis O4 and fifth axis O5, the position of the imaging device 106 in the vertical direction is changed. Therefore, by the rotation of the distal end (the end where the imaging device 106 is provided) of the arm 104 about the fourth axis O4 and fifth axis O5, the distance between the imaging device 106 and an observation target, such as a site of surgical operation in a patient, is able to be changed.

The link 112e is a member formed of a combination of: a first member substantially having an L-shape with one side thereof extending in a vertical direction and another side thereof extending in a horizontal direction; and a second member, which extends vertically downward from a portion of the first member, the portion extending in the horizontal direction, and which is rod-shaped. the joint 110e is fixedly connected to a portion of the first member of the link 112e, the portion extending in the vertical direction. Furthermore, the second member of the link 112e has the joint 110f connected thereto.

The joint 110f has a substantially columnar shape, and supports the link 112e rotatably about the rotation axis (the sixth axis O6) parallel to the vertical direction. Furthermore, the joint 110f has the link 112f fixedly connected thereto.

The link 112f is a member that is substantially rod shaped, and is extended in the vertical direction. The joint 110f is connected to one end of the link 112f. Furthermore, the other end (an end opposite to the end connected to the joint 110f) of the link 112f is fixedly connected to the base 102.

By the arm 104 having the above described configuration, in the medical observation apparatus 100, six degrees of freedom are realized with respect to movement of the imaging device 106.

The configuration of the arm 104 is not limited to the example described above.

For example, the joints 110a, 110b, 110c, 110d, 110e, and 110f of the arm 104 may respectively have brakes provided therein, the brakes respectively restricting rotation at the joints 110a, 110b, 110c, 110d, 110e, and 110f. Examples of the brakes according to the embodiment include brakes of any form, such as brakes that are mechanically driven, and electromagnetic brakes that are electrically driven.

Driving of the brakes is controlled by, for example, the processor that functions as the control unit described later, or the external medical control device (not illustrated in the drawings). By the control of the driving of the brakes, in the medical observation apparatus 100, operation modes of the arm 104 are set. Examples of the operation modes of the arm 104 include a fixed mode and a free mode.

The fixed mode according to the embodiment is an operation mode where, for example, the position and posture (the position and posture of an imaging unit 150 described later) of the imaging device 106 are fixed by restriction of rotation about the rotation axes provided in the arm 104 by means of the brakes. By the arm 104 being brought into the fixed mode, a state of operation of the medical observation apparatus 100 is brought into a fixed state where the position and posture of the imaging device 106 are fixed.

Furthermore, the free mode according to the embodiment is an operation mode where the rotation axes provided in the arm 104 are freely rotatable by the brakes being released. For example, in the free mode, the position and posture (the position and posture of the imaging unit 150 described later) of the imaging device 106 are allowed to be adjusted through direct manipulation by a surgical operator. The direct manipulation according to the embodiment means, for example, manipulation where a surgical operator holds the imaging device 106 in the hand and directly moves the imaging device 106.

[1-1-2-3] Imaging Device 106

The imaging device 106 is supported by the arm 104, and captures an image of an observation target, such as, for example, a site of surgical operation of a patient. Imaging in the imaging device 106 is controlled by, for example, the processor that functions as the control unit described later, or the external medical control device (not illustrated in the drawings).

The imaging device 106 has a configuration corresponding to, for example, an electronic imaging microscope.

Figure 3:
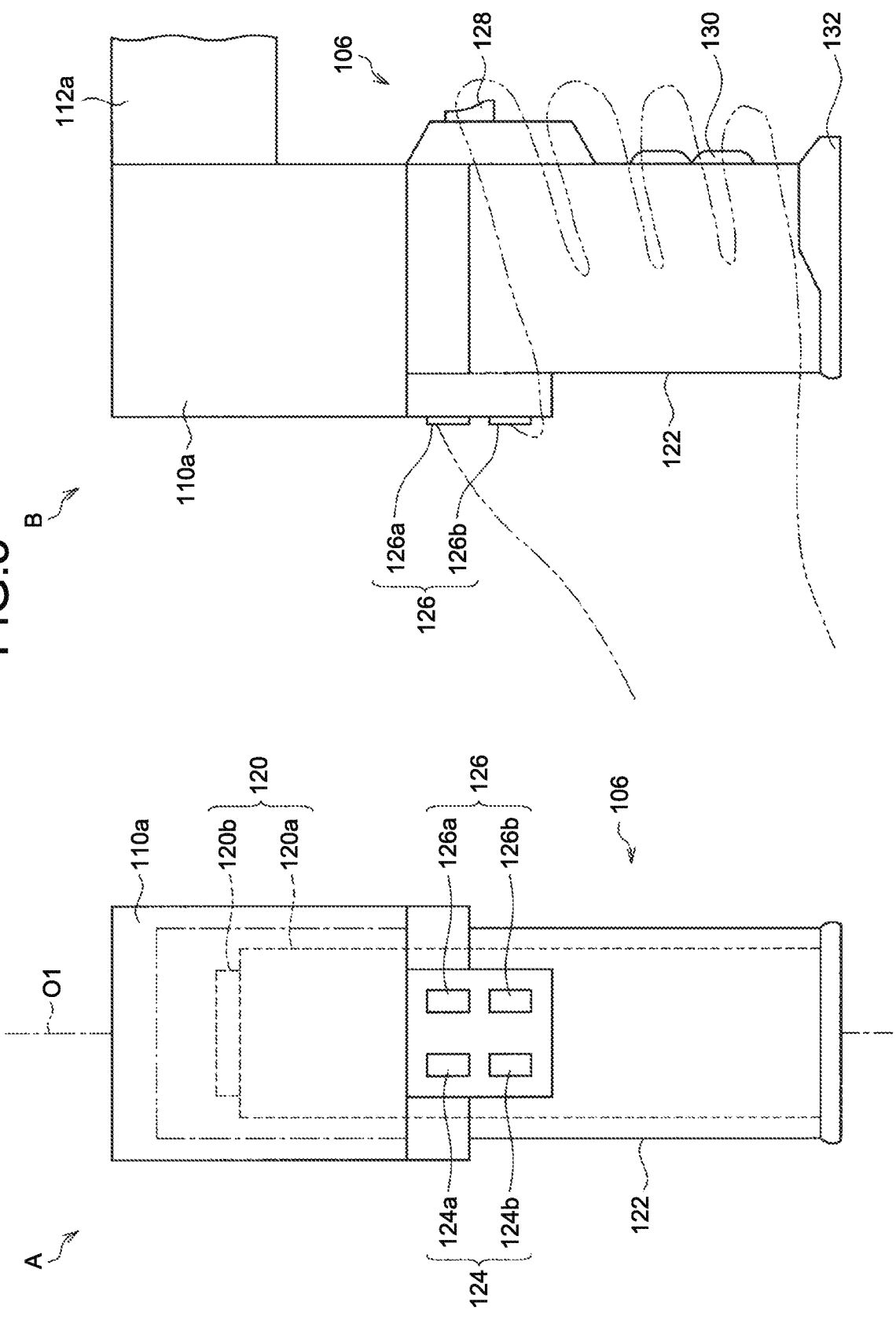
FIG. 3 is an explanatory diagram for explanation of an example of a configuration of an imaging device included in a medical observation apparatus according to the embodiment.

FIG. 3 is an explanatory diagram for explanation of an example of the configuration of the imaging device 106 included in the medical observation apparatus 100 according to the embodiment.

The imaging device 106 has, for example, an imaging member 120, and a cylindrical member 122 having a substantially cylindrical shape, and the imaging member 120 is provided in the cylindrical member 122.

On a plane of an opening at a lower end of the cylindrical member 122 (a lower end in FIG. 3), for example, a cover glass (not illustrated in the drawings) for protecting the imaging member 120 is provided.

Furthermore, for example, a light source (not illustrated in the drawings) is provided inside the cylindrical member 122, and at the time of imaging, illumination light is emitted from the light source to a subject through the cover glass. Reflected light (observation light) from the subject irradiated with the illumination light enters the imaging member 120 via the cover glass (not illustrated in the drawings), and an image signal representing the subject (an image signal representing a captured medical image) is thereby acquired by the imaging member 120.

Any one of configurations used in various known electronic imaging microscopes may be adopted for the imaging member 120.

For example, the imaging member 120 is formed of, for example: an optical system 120a; and an image sensor 120b including an imaging element that captures an image of an observation target by means of light that has passed through the optical system 120a. The optical system 120a is formed of, for example: one or more of lenses including an objective lens, a zoom lens, and a focus lens; and an optical element, such as a mirror. Examples of the image sensor 120b include an image sensor having plural imaging elements used therein, the imaging elements being, for example, complementary metal oxide semiconductors (CMOSs) or charge coupled devices (CCDs).

The imaging member 120 functions as a so-called stereo camera by including, for example, two or more imaging devices each formed of the optical system 120a and the image sensor 120b. In a configuration of the imaging device 106 that functions as the stereo camera, the optical system may be a Galilean optical system, or a Greenough-type optical system.

A case where the medical observation apparatus 100 according to the embodiment including the medical observation apparatus 100 forming a medical observation system according to a second example described later includes plural imaging devices that function as a stereo camera, and plural captured medical images including a captured right eye medical image and a captured left eye medical image are respectively acquired by imaging of the plural imaging devices will be described below as an example. Hereinafter, an imaging device that captures a captured right eye medical image will be referred to as a "first imaging device", and an imaging device that captures a captured left eye medical image will be referred to as a "second imaging device". Furthermore, hereinafter, a captured right eye medical image and a captured left eye medical image may be collectively referred to as "captured medical images".

The imaging devices forming the imaging member 120 are each installed with one or more functions generally included in an electric imaging microscope, such as a zoom function (one or both of an optical zoom function and an electronic zoom function) and an auto-focus (AF) function.

Furthermore, the imaging member 120 may be configured to enable imaging at so-called high-definition, for example, 4K or 8K. By the imaging member 120 being configured to enable high definition imaging, display of an image by the display device 200 including a large display screen of, for example, 50 inches or more, is enabled with predetermined definition (for example, full HD image quality) ensured, and thus visual recognizability by a surgical operator looking at the display screen is improved. Moreover, by the imaging member 120 being configured to enable high definition imaging, predetermined definition is able to be ensured even if an image captured is displayed enlarged by the electronic zoom function on the display screen of the display device 200. In addition, when predetermined definition is ensured by use of the electronic zoom function, performance of the optical zoom function in the imaging device 106 is able to be reduced, and thus the optical system of the imaging device 106 is able to be simplified more, and the imaging device 106 is able to be downsized.

The imaging device 106 is provided with, for example, various manipulation devices for controlling the operation of the imaging device 106. For example, in FIG. 3, a zoom switch 124, a focus switch 126, and an operation mode changing switch 128 are provided in the imaging device 106. Needless to say, the positions and forms where the zoom switch 124, the focus switch 126, and the operation mode changing switch 128 are provided are not limited to the example illustrated in FIG. 3.

The zoom switch 124 and the focus switch 126 are examples of the manipulation devices for adjusting imaging conditions in the imaging device 106.

The zoom switch 124 is formed of, for example, a zoom-in switch 124a that increases the zoom magnification (the magnifying power), and a zoom-out switch 124b that decreases the zoom magnification. By manipulation of the zoom switch 124, the zoom magnification is adjusted and zooming is adjusted.

The focus switch 126 is formed of, for example, a distant view focus switch 126a that increases the focal distance to an observation target (a subject), and a near view focus switch 126b that decreases the focal distance to the observation target. By the manipulation of the focus switch 126, the focal distance is adjusted and focusing is adjusted.

The operation mode changing switch 128 is an example of a manipulation device for changing the operation mode of the arm 104 in the imaging device 106. By manipulation of the operation mode changing switch 128, the operation mode of the arm 104 is changed. Examples of the operation mode of the arm 104 include, as described above, the fixed mode and the free mode.

Examples of the manipulation of the operation mode changing switch 128 include manipulation where the operation mode changing switch 128 is pressed down. For example, while a surgical operator is holding the operation mode changing switch 128 down, the operation mode of the arm 104 is in the free mode, and when the surgical operator is not holding the operation mode changing switch 128 down, the operation mode of the arm 104 is in the fixed mode.

Furthermore, the imaging device 106 is provided with, for example, a non-slip member 130 and a protruding member 132, for further improvement in operability and convenience upon manipulation by an operator performing manipulation of the various manipulation devices.

The non-slip member 130 is a member provided for prevention of slippage of a manipulating body, such as a hand, when, for example, the operator performs manipulation of the cylindrical member 122 with the manipulating body. For example, the non-slip member 130 is formed of a material having a large friction coefficient, and has a less slippery structure, such as bumps and dips.

The protruding member 132 is a member provided for prevention of: the manipulating body, such as the hand, blocking the field of view of the optical system 120a when the operator manipulates the cylindrical member 122 with the manipulating body; and the cover glass (not illustrated in the drawings) becoming unclean by the manipulating body touching the cover glass when manipulation with the manipulating body is performed.

Needless to say, positions and forms where the non-slip member 130 and protruding member 132 are respectively provided are not limited to the example illustrated in FIG. 3. Furthermore, the imaging device 106 may be not provided with one or both of the non-slip member 130 and the protruding member 132.

An image signal (image data) generated by imaging in the imaging device 106 is subjected to image processing in, for example, the processor functioning as the control unit described later. Examples of the image processing according to the embodiment include one or more of: gamma correction, white balance adjustment, image enlargement or reduction related to the electronic zoom function, and correction among pixels.

If the medical observation system according to the embodiment has the medical control device (not illustrated in the drawings) that controls various types of operation in the medical observation apparatus 100, the image processing according to the embodiment may be performed in the medical control device (not illustrated in the drawings).

The medical observation apparatus 100 transmits, for example, a display control signal, and an image signal subjected to image processing as mentioned above, to the display device 200.

By the transmission of the display control signal and image signal to the display device 200, a captured medical image having an observation target captured therein (for example, a captured image having a site of surgical operation captured therein) is displayed on the display screen of the display device 200. Upon this display, the captured medical image having the observation target captured therein may be displayed enlarged or reduced to a desired magnification by one or both of the optical zoom function and electronic zoom function, on the display screen of the display device 200.

The medical observation apparatus 100 illustrated in FIG. 1 has, for example, the hardware configuration described above by reference to FIG. 1 and FIG. 3.

The hardware configuration of the medical observation apparatus according to the embodiment is not limited to the configuration described above by reference to FIG. 1 and FIG. 3.

For example, the medical observation apparatus according to the embodiment may be configured to have the arm 104 directly attached to a ceiling or wall surface of a surgical operating room, without including the base 102. For example, if the arm 104 is attached to the ceiling, the medical observation apparatus according to the embodiment has a configuration where the arm 104 is suspended from the ceiling.

Furthermore, FIG. 1 illustrates the example where the arm 104 is configured to realize six degrees of freedom with respect to driving of the imaging device 106, but the configuration of the arm 104 is not limited to the configuration where the number of degrees of freedom related to the driving of the imaging device 106 is six. For example, the arm 104 may just be configured to be able to move the imaging device as appropriate according to a use, and the number and arrangement of the joints and links, and the directions of the drive axes of the joints may be set as appropriate such that the arm 104 has desired freedom.

Furthermore, FIG. 1 and FIG. 3 illustrate the example where the various manipulation devices for controlling the operation of the imaging device 106 are provided in the imaging device 106, but a part or all of the manipulation devices illustrated in FIG. 1 and FIG. 3 may be not provided in the imaging device 106. For example, the various manipulation devices for controlling the operation of the imaging device 106 may be provided in another part forming the medical observation apparatus according to the embodiment, instead of in the imaging device 106. Moreover, in another example, the various manipulation devices for controlling the operation of the imaging device 106 may include an external manipulation device, such as a foot switch FS or a remote controller.

Furthermore, the imaging device 106 may be configured to enable switch-over among plural observation modes. Examples of the observation modes according to the embodiment include: an observation mode where imaging is performed with natural light; an observation mode where imaging is performed with special light; and an observation mode where imaging is performed by use of an image enhancement observation technique, such as narrow band imaging (NBI). Examples of the special light according to the embodiment include light of specific wavelength bands, such as: light of a near infra-red wavelength band; and light of a fluorescent wavelength band of fluorescent observation where 5-aminolevulinic acid (5-ALA) is used.

Examples of the configuration of the imaging device 106, the configuration enabling the plural observation modes to be switched from one to another, include "a configuration including a filter that transmits therethrough light of a specific wavelength band and does not transmit therethrough light of other wavelength bands, and a moving mechanism that selectively places the filter onto an optical path". Examples of the specific wavelength band transmitted through the filter according to the embodiment include: a near infra-red wavelength band (for example, a wavelength band from about 0.7 micrometers to about 2.5 micrometers); a fluorescent wavelength band according to fluorescent observation by use of 5-ALA (for example, a wavelength band from about 0.6 micrometers to about 0.65 micrometers); and a fluorescent wavelength band of indocyanine green (ICG) (for example, a wavelength band from about 0.82 micrometers to about 0.85 micrometers).

The imaging device 106 may be provided with plural filters where wavelength bands transmitted therethrough are different from one another. Furthermore, the above description is on the example where imaging is performed with light of a specific wavelength band by the arrangement of the filter on the optical path, but needless to say, the configuration of the imaging device 106 for imaging with light of a specific wavelength band is not limited to the above described example.

[1-2] Medical Observation System According to Second Example

The medical observation system 1000 according to the embodiment is not limited to the configuration represented by the first example illustrated in FIG. 1. An example of the configuration of a medical observation system 1000 including a medical observation apparatus 100 that functions as an endoscope apparatus will be described next as another example of the medical observation system 1000.

Figure 4:
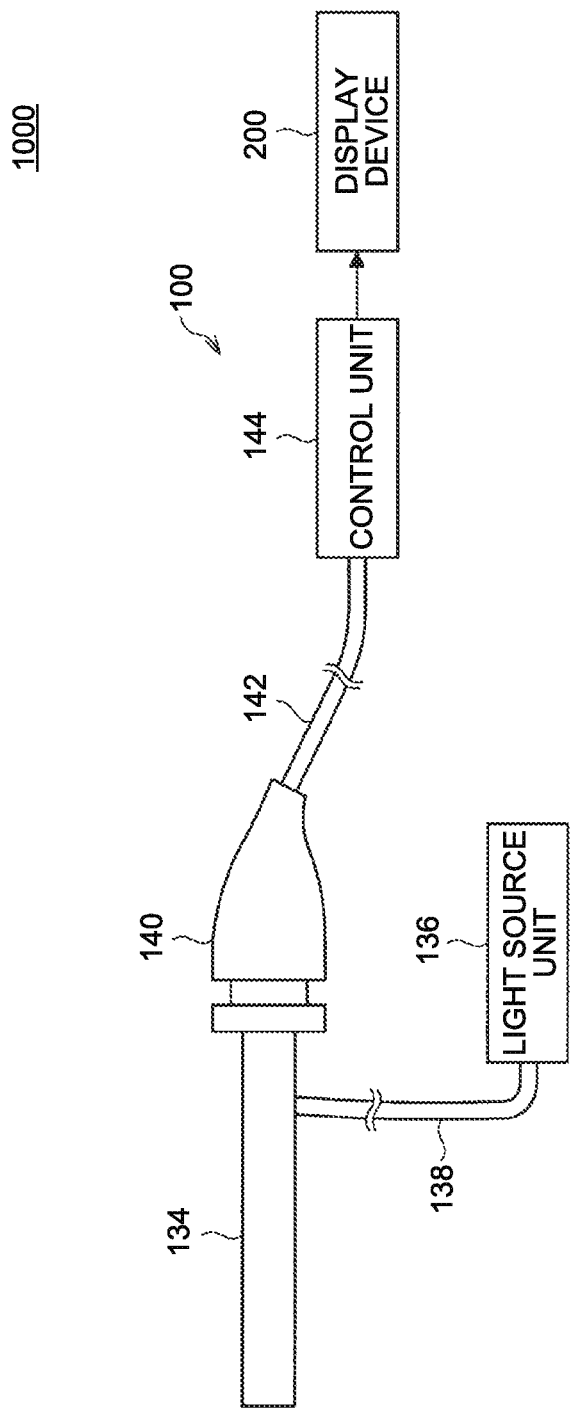
FIG. 4 is an explanatory diagram illustrating a second example of the configuration of the medical observation system according to the embodiment.

FIG. 4 is an explanatory diagram illustrating a second example of the configuration of the medical observation system 1000 according to the embodiment. The medical observation system 1000 illustrated in FIG. 4 has, for example, the medical observation apparatus 100 and the display device 200. For example, if the medical observation apparatus 100 illustrated in FIG. 4 is used in a surgical operation, a surgical operator observes a site of surgical operation while referring to a captured medical image captured by the medical observation apparatus 100 and displayed on the display screen of the display device 200, and performs various treatments, such as maneuvers according to operative surgical procedures, on the site of surgical operation.

The medical observation system according to the second example is not limited to the example illustrated in FIG. 4.

For example, similarly to the medical observation system according to the first example, the medical observation system according to the second example may further have a medical control device (not illustrated in the drawings) that controls various types of operation in the medical observation apparatus 100.

Furthermore, similarly to the medical observation system according to the first example, the medical observation system according to the second example may be configured to have plural medical observation apparatuses 100, plural display devices 200, or both plural medical observation apparatus 100 and plural display devices 200.

Each device forming the medical observation system 1000 according to the second example illustrated in FIG. 4 will be described below.

[1-2-1] Display Device 200

The display device 200 is a display means in the medical observation system 1000 according to the second example, and corresponds to a display device external to the medical observation apparatus 100. The display device 200 forming the medical observation system 1000 according to the second example is similar to the display device 200 forming the medical observation system 1000 according to the first example.

[1-2-2] Medical Observation Apparatus 100

The medical observation apparatus 100 illustrated in FIG. 4 includes, for example, an insertion member 134, a light source unit 136, a light guide 138, a camera head 140, a cable 142, and a control unit 144. The medical observation apparatus 100 is driven by, for example, electric power supplied from an internal power source, such as a battery, which is included in the medical observation apparatus 100, or electric power supplied from an external power source connected to the medical observation apparatus 100.

The insertion member 134 has an elongated shape, and includes therein an optical system that condenses incident light. A distal end of the insertion member 134 is inserted into, for example, a body cavity of a patient. A rear end of the insertion member 134 is attachably and detachably connected to a distal end of the camera head 140. Furthermore, the insertion member 134 is connected to the light source unit 136 via the light guide 138, and light from the light source unit 136 is supplied to the insertion member 134.

The insertion member 134 may be, for example, formed of a material not having flexibility, or formed of a material having flexibility. The medical observation apparatus 100 may be called a rigid endoscope or a flexible endoscope, depending on the material forming the insertion member 134.

The light source unit 136 is connected to the insertion member 134 via the light guide 138. The light source unit 136 supplies light to the insertion member 134 via the light guide 138.

The light source unit 136 has, for example, plural light sources that emit light of different wavelengths. Examples of the plural light sources that the light source unit 136 has include: a light source that emits red light, a light source that emits green light, and a light source that emits blue light. The light source that emits red light may be, for example, one or more red light emitting diodes. The light source that emits green light may be, for example, one or more green light emitting diodes. The light source that emits blue light may be, for example, one or more blue light emitting diodes. Needless to say, the plural light sources that the light source unit 136 has are not limited to the above described examples. For example, the light source unit 136 may have the plural light sources on a single chip, or may have the plural light sources on plural chips.

The light source unit 136 is connected wiredly or wirelessly to the control unit 144, and light emission in the light source unit 136 is controlled by the control unit 144.

Light supplied to the insertion member 134 is emitted from the distal end of the insertion member 134, and an observation target, such as a tissue in a body cavity of a patient, is irradiated with the emitted light. Reflected light from the observation target is condensed by the optical system in the insertion member 134.

The camera head 140 has a function of capturing an image of an observation target. The camera head 140 is connected to the control unit 144 via the cable 142, which is a signal transmission member.

The camera head 140 has an image sensor, captures an image of an observation target by photoelectrically converting reflected light from the observation target, the reflected light having been condensed by the insertion member 134, and outputs an image signal (a signal representing a captured medical image) acquired by imaging, to the control unit 144 via the cable 142. The image sensor that the camera head 140 has may be, for example, an image sensor having, used therein, plural imaging elements, such as CMOSs or CCDs.

In the medical observation apparatus 100 that functions as an endoscope apparatus, for example, the insertion member 134, the light source unit 136, and the camera head 140 serve as "an imaging device that is inserted into a body of a patient and captures an image of the interior of the body".

The medical observation apparatus 100 that functions as an endoscope apparatus includes, for example, plural imaging devices that function as a so-called stereo camera. In a configuration of each of the imaging devices that function as the stereo camera, similarly to the medical observation apparatus 100 forming the medical observation system according to the first example, the optical system may be a Galilean optical system, or a Greenough-type optical system.

The control unit 144 controls the imaging devices. More specifically, the control unit 144 controls each of the light source unit 136 and the camera head 140.

Furthermore, the control unit 144 includes a communication device (not illustrated in the drawings), and transmits an image signal output from the camera head 140, to the display device 200 by arbitrary wireless communication or arbitrary wired communication. The control unit 144 may transmit an image signal and a display control signal, to the display device 200.

The communication device (not illustrated in the drawings) included in the control unit 144 may be, for example: an IEEE 802.15.1 port and a transmitting and receiving circuit (wireless communication); an IEEE 802.11 port and a transmitting and receiving circuit (wireless communication); a communication antenna and an RF circuit (wireless communication); an optical communication device (wired communication or wireless communication); or a LAN terminal and a transmitting and receiving circuit (wired communication). The communication device (not illustrated in the drawings) may be configured to be able to perform communication with one or more external devices by plural communication methods.

Furthermore, the control unit 144 may perform predetermined processing on an image signal output to the camera head 140, and transmit the image signal that has been subjected to the predetermined processing, to the display device 200. Examples of the predetermined processing on the image signal include: white balance adjustment, image enlargement or reduction related to an electronic zoom function, and correction among pixels.

The control unit 144 may store therein a captured medical image that is based on an image signal.

The control unit 144 may be, for example, a camera control unit (CCU).

The medical observation apparatus 100 that functions as an endoscope apparatus has, for example, the hardware configuration described by reference to FIG. 4. In the medical observation apparatus 100 that functions as an endoscope apparatus, for example, the insertion member 134, the light source unit 136, and the camera head 140 serve as an imaging device, and imaging in the imaging device is controlled by the control unit 144.

[1-3] Functional Configuration of Medical Observation Apparatus 100

Figure 5:
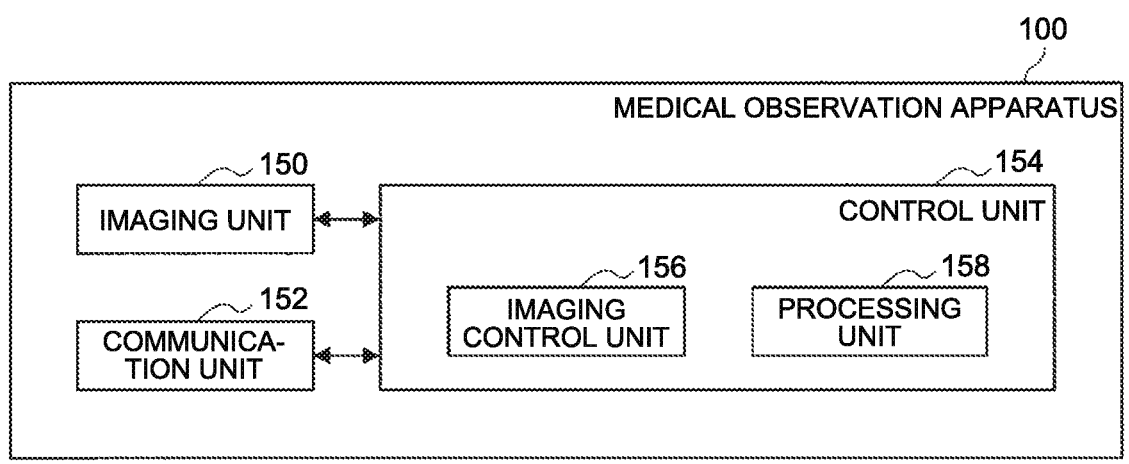
FIG. 5 is a functional block diagram illustrating an example of a configuration of the medical observation apparatus according to the embodiment.

The medical observation apparatuses 100 illustrated in FIG. 1 and FIG. 4 will be described by use of functional blocks next. FIG. 5 is a functional block diagram illustrating an example of a configuration of the medical observation apparatus 100 according to the embodiment.

The medical observation apparatus 100 includes, for example, the imaging unit 150, a communication unit 152, and a control unit 154.

The imaging unit 150 captures an image of an observation target. The imaging unit 150 is formed of, for example, "the imaging device 106" (for the medical observation apparatus 100 illustrated in FIG. 1), or "the insertion member 134, the light source unit 136, and the camera head 140" (for the medical observation apparatus 100 illustrated in FIG. 4). Imaging in the imaging unit 150 is controlled by, for example, the control unit 154.

The communication unit 152 is a communication means included in the medical observation apparatus 100, and plays a role of performing communication wirelessly or wiredly with an external device, such as the display device 200. The communication unit 152 is formed of, for example, the above described communication device (not illustrated in the drawings). Communication in the communication unit 152 is controlled by, for example, the control unit 154.

The control unit 154 is formed of, for example, the above described processor (not illustrated in the drawings), and plays a role of controlling the whole medical observation apparatus 100. Furthermore, the control unit 154 plays a role of proactively performing processing related to the display control method described later. The processing related to the display control method in the control unit 154 may be distributed and performed among plural processing circuits (for example, plural processors) More specifically, the control unit 154 has, for example, an imaging control unit 156 and a processing unit 158.

The imaging control unit 156 controls the imaging device forming the imaging unit 150. The control of the imaging device may be, for example, control of one or more functions generally included in an electronic imaging microscope, such as control of the zoom functions (the optical zoom function and electronic zoom function) and the AF function.

The processing unit 158 performs the processing related to the later described display control method according to the embodiment. An example of a functional configuration of the processing unit 158, and an example of the processing related to the display control method according to the embodiment will be described later.

By including, for example, the processing unit 158, the control unit 154 plays a role of proactively performing the processing related to the display control method according to the embodiment. Furthermore, by including, for example, the imaging control unit 156 and the processing unit 158, the control unit 154 plays a role of controlling the whole medical observation apparatus 100.

The functional configuration of the control unit 154 is not limited to the example illustrated in FIG. 5.

For example, the control unit 154 may have any configuration according to a way in which functions that the medical observation apparatus 100 has are divided, such as a configuration according to a way in which the processing related to the display control method according to the embodiment is divided.

For example, if the medical observation apparatus 100 has the configuration illustrated in FIG. 1, the control unit 154 may further have an arm control unit (not illustrated in the drawings) that controls driving of the arm 104. For example, the control of the driving of the arm 104 may be "application of control signals that control driving, to the actuators (not illustrated in the drawings) respectively corresponding to the joints 110*a*, 110*b*, 110*c*, 110*d*, 110*e*, and 110*f*".

The medical observation apparatus 100 performs the processing related to the later described display control method according to the embodiment by means of, for example, the functional configuration illustrated in FIG. 5.

The functional configuration of the medical observation apparatus according to the embodiment is not limited to the configuration illustrated in FIG. 5.

For example, the medical observation apparatus according to the embodiment may include one or both of the imaging control unit 156 and processing unit 158 both illustrated in FIG. 5, individually from the control unit 154 (for example, by realization of one or both of them by means of another processing circuit).

Furthermore, the functional configuration that enables execution of the processing related to the display control method according to the embodiment in the medical observation apparatus according to the embodiment is not limited to the configuration illustrated in FIG. 5, and for example, the medical observation apparatus according to the embodiment may have a functional configuration according to a way in which the processing related to the display control method according to the embodiment is divided.

Furthermore, if the medical observation apparatus according to the embodiment has the configuration illustrated in FIG. 1, the medical observation apparatus according to the embodiment has an arm unit (not illustrated in the drawings) formed of the arm 104. The arm 104 forming the arm unit (not illustrated in the drawings) supports the imaging device 106 that forms the imaging unit 150.

Furthermore, for example, if communication is performed with an external device via an external communication device having functions and a configuration similar to those of the communication unit 152, the medical observation apparatus according to the embodiment may be provided without the communication unit 152.

Furthermore, if the medical observation system according to the embodiment is configured to have the medical control device (not illustrated in the drawings), and the medical observation apparatus according to the embodiment is controlled by the medical control device (not illustrated in the drawings), the medical observation apparatus according to the embodiment may be provided without the control unit 154.

For example, the medical control device (not illustrated in the drawings) performs the processing related to the later described display control method according to the embodiment by including a control unit having functions and a configuration similar to those of the control unit 154, and controls operation in each component, such as the imaging unit 150 included in the medical observation apparatus according to the embodiment. The medical control device (not illustrated in the drawings) controls operation in each component included in the medical observation apparatus according to the embodiment by performing communication with the medical observation apparatus according to the embodiment via a communication device included in the medical control device or an external communication device connected to the medical control device.

Furthermore, if the medical observation system according to the embodiment is configured to have the medical control device (not illustrated in the drawings), and the medical observation apparatus according to the embodiment is controlled by the medical control device (not illustrated in the drawings), the medical observation apparatus according to the embodiment may be configured without a part of the functions of the control unit 154.

[2] Display Control Method According to Embodiment

The display control method according to the embodiment will be described next. Hereinafter, a case where the medical observation apparatus 100 performs the processing related to the display control method according to the embodiment will be described as an example. As described above, in the medical observation system according to the embodiment, the processing related to the display control method according to the embodiment may be performed by the medical control device (not illustrated in the drawings).

[2-1] Outline of Display Control Method According to Embodiment

In a surgical operation (a so-called microsurgery) performed by use of the medical observation apparatus 100, for example, like in an example described below, measurement of a length of a lesion in the field of view for observation by a surgical operator may be needed.

In surgical clipping for a cerebral aneurysm performed by use of the medical observation apparatus 100 illustrated in FIG. 1, for an optimum clip to be selected, measurement of a length of a lesion is needed, the optimum clip corresponding to the shape and length of a neck region of a cerebral aneurysm.

In a laparoscopic (abdominal incisional) hernia surgical operation performed by use of the medical observation apparatus 100 illustrated in FIG. 4 (for example, a rigid endoscope), for trimming in a mesh shape that closes a hernial orifice and provides a sufficient overlapping region, measurement of a length of the hernial orifice is needed.

In an arthroscopic rotator cuff repair surgical operation performed by use of the medical observation apparatus 100 illustrated in FIG. 4 (for example, a rigid endoscope) and by use of a patching method for a rotator cuff tear, for determination of a size of a fascia patch necessary for repair of a torn region of a rotator cuff, measurement of a length of the torn region is needed.

In such cases, in medical settings, lengths of lesions may be measured by use of measuring tapes. However, in this method where measurement is performed by use of a measuring tape, for example, maneuvers are stopped by insertion of the measuring tape in a lesion region, and labor, such as disposal or cleaning of the measuring tape, is generated, and thus this method is hardly a convenient measuring method.

Furthermore, since there is no convenient measuring method for measurement of a length of a lesion when measurement of the length is needed, the length is sometimes estimated by a surgical operator relying on experience and feeling instead of performing measurement. However, an estimate by experience and feeling doe not necessarily enable accurate measurement of a length of a lesion. Furthermore, in, for example, surgical clipping for a cerebral aneurysm, if the estimation accuracy of the length is low, a process of trial and error is caused in the selection of a clip, for example, and thus undesired circumstances, such as waste of clips and increase in the risk of damage in the aneurysm, may be caused.

The medical observation apparatus 100 thus causes an annotation image to be displayed on the display screen of the display device 200, the annotation image indicating a distance between positions of two points in an observation target. Hereinafter, a distance between positions of two points in an observation target may simply be referred to as a "distance between two points" The positions of the two points in the observation target are each acquired based on predetermined operation on the observation target.

The predetermined operation on the observation target includes, for example, operation where a predetermined medical tool, such as forceps, or a position detecting probe is moved into an imaging range of the imaging device 106 that functions as the imaging unit 150.

The positions in the observation target, the positions being based on the predetermined medical tool, are, for example, acquired by "detection of the predetermined medical tool from one or both of a captured right eye medical image and a captured left eye medical image", that is, "detection of an object corresponding to the predetermined operation, from one or both of the captured right eye medical image and the captured left eye medical image". The detection of the object corresponding to the predetermined operation from the captured medical image/images is performed by, for example, any image processing that enables an object to be detected from an image, such as detection by pattern matching. A position of a specific portion of the object detected from the captured medical image/images (for example, a position of a distal end portion of forceps) corresponds to a position acquired based on the predetermined operation on the observation target.

By detection of an object from one of a captured right eye medical image and a captured left eye medical image, a position in a plane corresponding to that captured medical image is determined as a position in an observation target. In this determination, the position in the observation target is represented by two-dimensional coordinates having an arbitrary position as the origin.

Furthermore, by detection of an object from both of a captured right eye medical image and a captured left eye medical image, a spatial position corresponding to the captured medical images is determined as a position in an observation target. In this determination, the position in the observation target is represented by three-dimensional coordinates having an arbitrary position as the origin.

One or both of image processing related to the above described detection and image processing related to the determination of a position may be performed by the medical observation apparatus 100, or may be performed in a device, such as the medical control device (not illustrated in the drawings), which is external to the medical observation apparatus 100. Furthermore, the image processing related to the detection and the image processing related the determination of a position may be performed by the medical observation apparatus 100 and the external device in cooperation with each other.

A position in an observation target, the position being based on the position detecting probe, is acquired by, for example, "detection of a spatial position of the position detecting probe by the above described navigation device". If a result of the detection in the navigation device is used, the medical observation apparatus 100 determines, as the position in the observation target, a spatial position indicated by positional information, by acquiring the positional information from the navigation device (an example of a detecting device that detects a position in an observation target). In this case, because the medical observation apparatus 100 does not need to perform the image processing related to the detection and the image processing related to the determination of the position, the processing load in the medical observation apparatus 100 is reduced, and the configuration of the medical observation apparatus 100 is able to be simplified.

For example, a distance between two points corresponding to positions of two points determined as described above is acquired by, for example, calculation of a Euclidean distance between the acquired positions of the two points. The distance between two points is not limited to the Euclidean distance, and may be a distance found by any method that enables representation of the distance between two points. The processing for the above described calculation of a distance may be performed by the medical observation apparatus 100, or may be performed in a device, such as the medical control device (not illustrated in the drawings), which is external to the medical observation apparatus 100.

Figure 6:
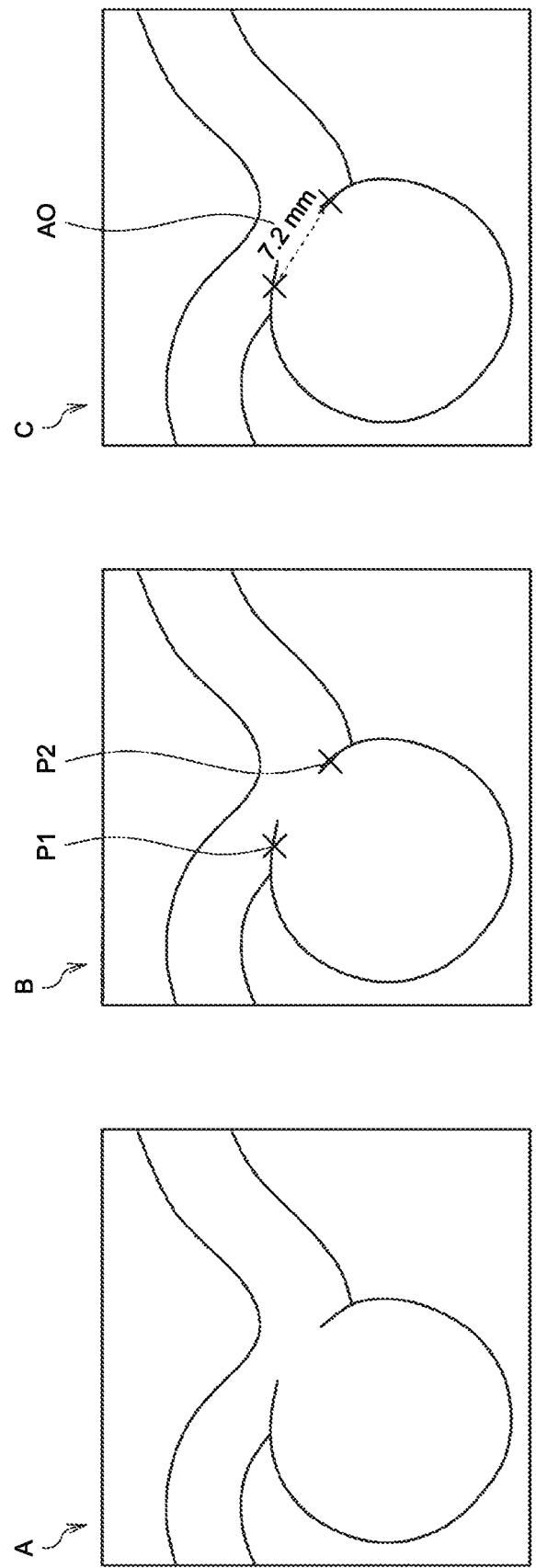
FIG. 6 is an explanatory diagram for explanation of an example of an annotation image displayed by a display control method according to the embodiment.
Figure 7:
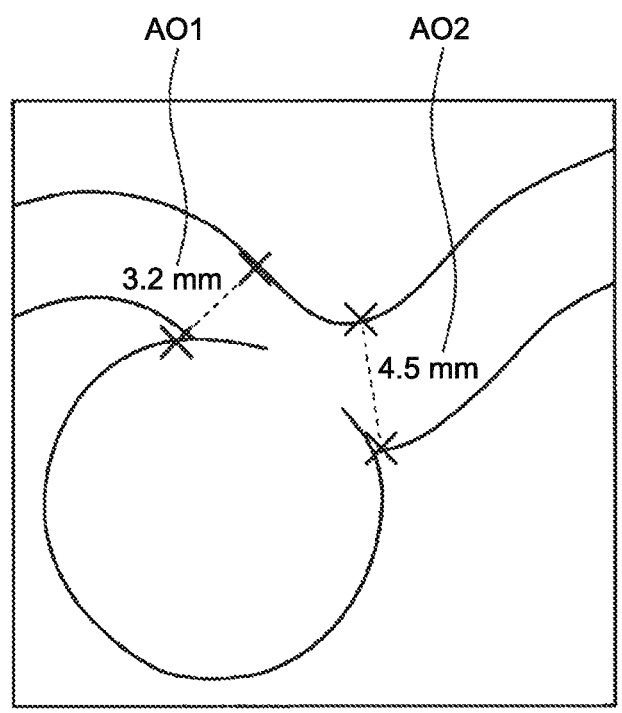
FIG. 7 is an explanatory diagram for explanation of another example of the annotation image displayed by the display control method according to the embodiment.

FIG. 6 is an explanatory diagram for explanation of an example of an annotation image displayed by the display control method according to the embodiment. FIG. 7 is an explanatory diagram for explanation of another example of the annotation image displayed by the display control method according to the embodiment.

In FIG. 6, "A" represents an example of a captured medical image before the annotation image is displayed. Examples of the captured medical image represented by "A" in FIG. 6 include one or both of a captured right eye medical image and a captured left eye medical image. In FIG. 6, "B" represents an example of positions acquired for the captured medical image represented by "A" in FIG. 6, and this example represented by "B" in FIG. 6 illustrates two positions P1 and P2. In FIG. 6, "C" represents an example of a captured medical image after an annotation image AO corresponding to the positions P1 and P2 illustrated in FIG. 6 has been displayed over the captured medical image represented by "A" in FIG. 6. FIG. 7 illustrate an example of a captured medical image after plural annotation images have been displayed over the captured medical image represented by "A" in FIG. 6, and in FIG. 7, an example where annotation images AO1 and AO2 have been displayed is illustrated.

For example, as represented by "C" in FIG. 6, when the display control method according to the embodiment is used, the medical observation apparatus 100 displays the annotation image AO superimposed on one or both of the captured right eye medical image and the captured left eye medical image. By the superimposition of the annotation image AO on the captured medical image as represented by "C" in FIG. 6, for example, a medical worker, such as a surgical operator, is able to visually recognize the length of a lesion in the field of view for observation.

Furthermore, as illustrated in FIG. 7, for example, when the display control method according to the embodiment is used, the medical observation apparatus 100 is able to display the plural annotation images AO1 and AO2 superimposed on one or both of the captured right eye medical image and the captured left eye medical image. The medical observation apparatus 100 displays the annotation images corresponding respectively to the acquired pairs of positions of two points, the annotation images having been superimposed on the captured medical image. By the superimposition of the plural annotation images AO1 and AO2 on the captured medical image as illustrated in FIG. 7, for example, a medical worker, such as a surgical operator, is able to visually recognize the lengths of plural lesions in the field of view for observation at once.

Examples of the annotation image according to the embodiment are not limited to images displaying numerical values of distances between two points, as represented by "C" in FIG. 6 and illustrated in FIG. 7. For example, the annotation image according to the embodiment may be "an image of a medical tool corresponding to a distance between two points, such as an image of a clip corresponding to a distance between two points", "a model number of a medical tool corresponding to a distance between two points", or "an image indicating a name of a medical tool corresponding to a distance between two points".

As described above, when the display control method according to the embodiment is used, an annotation image is displayed based on operation where a predetermined medical tool, such as forceps, is moved into the imaging range of the imaging device 106, or operation where the position detecting probe is moved into the imaging range of the imaging device 106. That is, when the display control method according to the embodiment is used, an annotation image is displayed by operation that is higher in relevance to ""medical intervention performed by a medical worker through use of the medical observation apparatus 100" than GUI manipulation is. Therefore, a possibility that medical intervention is interrupted by predetermined operation on an observation target according to the embodiment is lower than that in a case where GUI manipulation according to the technique described in Japanese Translation of PCT International Application, Publication No. 2007-521864 is performed.

Therefore, by use of the display control method according to the embodiment, convenience for a user of the medical observation apparatus 100 is able to be improved.

[2-2] Example of Processing Related to Display Control Method According to Embodiment An example of the processing related to the display control method according to the embodiment will be described below. Hereinafter, a case where the processing related to the display control method according to the embodiment is performed in the processing unit 158 illustrated in FIG. 4 will be described as an example.

[2-2-1] First Example of Processing According to Display Control Method

Figure 8:
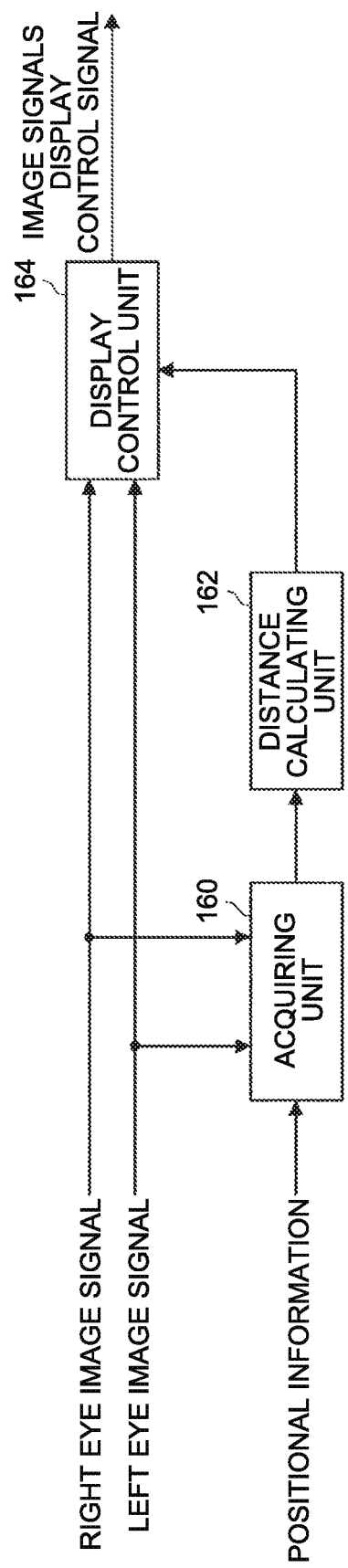
FIG. 8 is a functional block diagram illustrating a first example of a configuration of a processing unit included in the medical observation apparatus according to the embodiment.

FIG. 8 is a functional block diagram illustrating a first example of a configuration of the processing unit 158 included in the medical observation apparatus 100 according to the embodiment. A "right eye image signal" illustrated in FIG. 8 is an image signal representing a captured right eye medical image captured by a first imaging device (the same applying hereinafter to the other drawings). Furthermore, a "left eye image signal" illustrated in FIG. 8 is an image signal representing a captured left eye medical image captured by a second imaging device (the same applying hereinafter to the other drawings).

The processing unit 158 according to the first example has, for example, an acquiring unit 160, a distance calculating unit 162, and a display control unit 164.

The acquiring unit 160 acquires positions of at least two points in an observation target, the positions being determined based on predetermined operation on the observation target.

The acquiring unit 160 acquires the positions in the observation target by, for example, detecting an object corresponding to predetermined operation, from one or both of a captured right eye medical image and a captured left eye medical image, as described above. Furthermore, the acquiring unit 160 may acquire the positions in the observation target by, for example, acquiring positional information from a navigation device (an example of a detecting device, the same applying hereinafter) as described above.

The acquiring unit 160 transmits information indicating the acquired positions, to the distance calculating unit 162. The position indicating information may be, for example, data representing the two-dimensional coordinates, or data representing the three-dimensional space coordinates. When the positional information is acquired from the navigation device, the acquiring unit 160 may transmit, as the position indicating information, the positional information acquired from the navigation device, to the distance calculating unit 162, or may transmit, as the position indicating information, information resulting from some sort of processing on the positional information, to the distance calculating unit 162.

Figure 9:
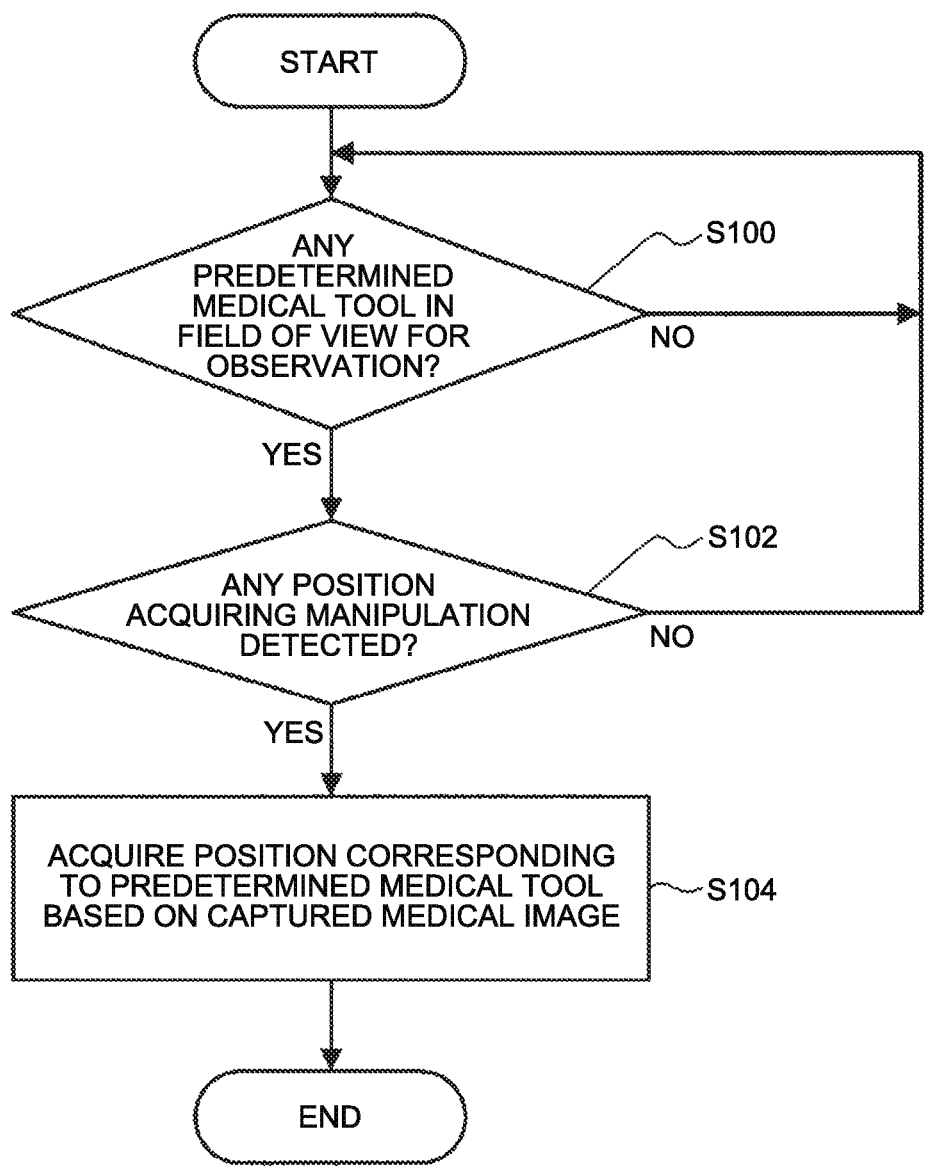
FIG. 9 is a flow chart illustrating an example of processing in an acquiring unit that the processing unit included in the medical observation apparatus according to the embodiment has.

FIG. 9 is a flow chart illustrating an example of processing in the acquiring unit 160 that the processing unit 158 included in the medical observation apparatus 100 according to the embodiment has. FIG. 9 illustrates an example of processing "in a case where positions in an observation target are acquired by detection of an object from a captured medical image, the object corresponding to predetermined operation".

The acquiring unit 160 determines whether or not a predetermined medical tool is in the field of view for observation (S100). If the predetermined medical tool has been detected by any image processing that enables detection of an object from an image, such as detection by pattern matching, for example, the acquiring unit 160 determines that the predetermined medical tool is in the filed of view.

If it is not determined that the predetermined medical tool is in the filed of view at Step S100, the acquiring unit 160 repeats Step S100.

Furthermore, if it is determined that the predetermined medical tool is in the field of view at Step S100, the acquiring unit 160 determines whether or not a position acquiring manipulation has been detected (S102).

The position acquiring manipulation may be any manipulation, for example, "a manipulation of a manipulation device included in the medical observation apparatus 100", "a manipulation of a manipulation device, such as a foot switch FS, which is external to the medical observation apparatus 100", "a manipulation through a gesture", or "a manipulation through voice".

If the position acquiring manipulation is a manipulation of a manipulation device included in the medical observation apparatus 100, or a manipulation of an external manipulation device, the acquiring unit 160 identifies the position acquiring manipulation, based on, for example, a manipulation signal corresponding to the manipulation.

If the position acquiring manipulation is a manipulation through gesture, the acquiring unit 160 identifies the position acquiring manipulation through gesture, based on, for example, "a gesture detection result of detection by arbitrary image processing on a captured image having a manipulation detection target captured therein". The image processing related to the gesture detection may be performed by the medical observation apparatus 100, or may be performed in a device external to the medical observation apparatus 100.

If the position acquiring manipulation is a manipulation through voice, the acquiring unit 160 identifies the position acquiring manipulation through voice, based on, for example, "a predetermined voice detection result of detection by arbitrary signal processing on voice acquired by a voice input device, such as a microphone". The voice input device may be a voice input device included in the medical observation apparatus 100, or a voice input device external to the medical observation apparatus 100. The signal processing related to the position acquiring manipulation for voice may be performed by the medical observation apparatus 100, or may be performed in a device external to the medical observation apparatus 100.

If it is not determined that a position acquiring manipulation has been detected at Step S102, the acquiring unit 160 repeats the processing from Step S100.

Furthermore, if it is determined that the position acquiring manipulation has been detected at Step S102, the acquiring unit 160 acquires positions corresponding to a predetermined medical tool, based on a captured medical image (S104).

The acquiring unit 160 acquires positions in an observation target by performing, for example, the processing illustrated in FIG. 9. As described above, the processing in the acquiring unit 160 is not limited to the example illustrated in FIG. 9.

A functional configuration of the processing unit 158 according to the first example will be described by reference to FIG. 8 again. The distance calculating unit 162 calculates, based on position indicating information transmitted from the acquiring unit 160, a distance corresponding to the acquired positions of two points. If plural pairs of positions of two points have been acquired by the acquiring unit 160, the distance calculating unit 162 calculates a distance corresponding to each of the acquired pairs of positions of two points. The distance calculating unit 162 calculates, for example, a Euclidean distance between two points.

The distance calculating unit 162 transmits information indicating the calculated distance between two points, to the display control unit 164. The position indicating information may be, for example, numerical data representing the distance. If plural distances between two points have been calculated, the distance calculating unit 162 transmits information indicating distances respectively corresponding to the pairs of positions of two points, to the display control unit 164. The information indicating distances may be, for example, numerical data representing the distances.

Figure 10:
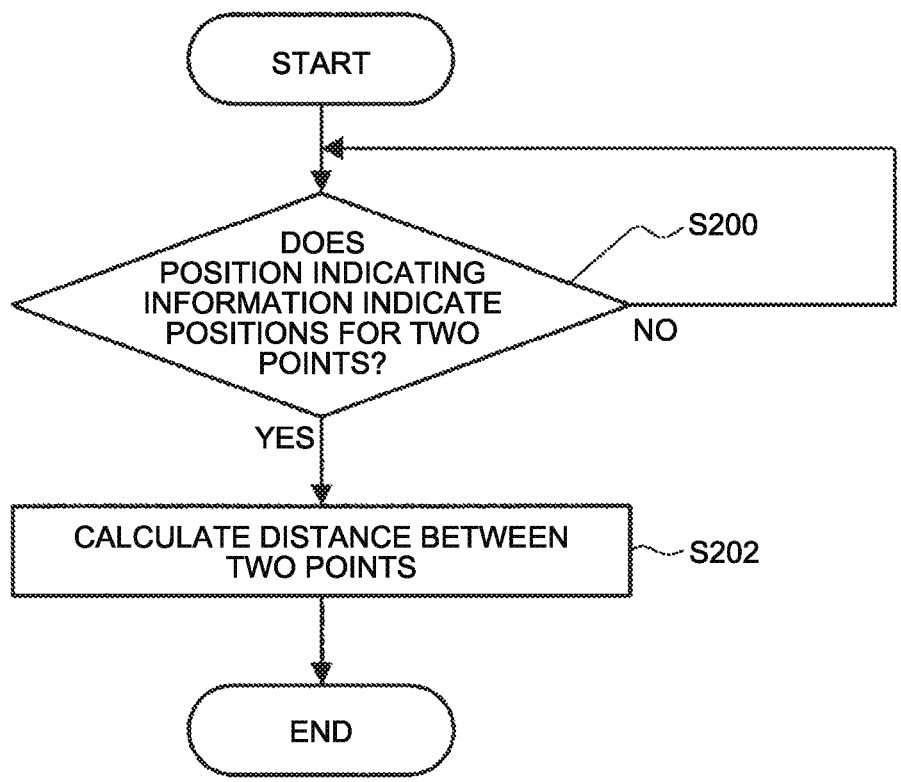
FIG. 10 is a flow chart illustrating an example of processing in a distance calculating unit that the processing unit included in the medical observation apparatus according to the embodiment has.

FIG. 10 is a flow chart illustrating an example of processing in the distance calculating unit 162 that the processing unit 158 included in the medical observation apparatus according to the embodiment has.

The distance calculating unit 162 determines whether or not position indicating information transmitted from the acquiring unit 160 indicates positions for two points (S200). For example, the distance calculating unit 162 sets a pair of positions of two points in the order that position indicating information is transmitted, and determines that the position indicating information indicates positions for two points when the pair of positions of two points has been set. Furthermore, if position indicating information includes identification information (for example, an ID) indicating a pair of positions of two points, the pair of positions of two points may be set according to the identification information, and the position indicating information may be determined to indicate positions for two points when the pair of positions of two points has been set.

If it is not determined that the position indicating information indicates positions for two points at Step S200, the distance calculating unit 162 repeats Step S200 until it is determined that the position indicating information indicates positions for two points.

Furthermore, if it is determined that the position indicating information indicates positions for two points at Step S200, the distance calculating unit 162 calculates a distance between the two points (S202).

For example, by performing the processing illustrated in FIG. 10, the distance calculating unit 162 calculates a distance corresponding to the acquired positions of two points. Needless to say, the processing in the distance calculating unit 162 is not limited to the example illustrated in FIG. 10.

A functional configuration of the processing unit 158 according to the first example will be described by reference to FIG. 8 again. The display control unit 164 causes a captured right eye medical image, a captured left eye medical image, and an annotation image, to be displayed on the display screen of the display device 200, the annotation image indicating a distance between two points having their positions acquired. In FIG. 8, for convenience, an image signal representing the captured right eye medical image output from the display control unit 164, an image signal representing the captured left eye medical image, and an image signal representing the annotation image are written as "image signals" (the same applying to the figures related to the processing unit 158 according to another example described later).

For example, the display control unit 164 reads an annotation image corresponding to information indicating a distance, from a recording medium (not illustrated in the drawings) that functions as a storage unit (not illustrated in the drawings), and causes the read annotation image to be displayed on the display screen of the display device 200. If information indicating distances respectively corresponding to pairs of positions of two points has been transmitted, that is, if plural pairs of positions of two points have been acquired, the display control unit 164 causes annotation images respectively corresponding to the distances between two points to be displayed on the display screen. An annotation image corresponding to information indicating a distance is identified by reference to a table (or a database) having distances and annotation images associated with each other.

The display control unit 164 causes an annotation image to be displayed superimposed on one or both of a captured right eye medical image and a captured left eye medical image, for example, as represented by "C" in FIG. 6 and illustrated in FIG. 7.

The processing unit 158 that performs the processing related to the display control method according to the first example causes an annotation image as represented by "C" in FIG. 6 or illustrated in FIG. 7 to be displayed with a captured medical image, by means of, for example, the functional configuration illustrated in FIG. 8.

The functional configuration of the processing unit according to the first example is not limited to the example illustrated in FIG. 8.

For example, in the processing unit 158 according to the first example, the display control unit 164 may have a function of the distance calculating unit 162.

Furthermore, if the processing in the distance calculating unit 162 is performed in a device external to the medical observation apparatus 100, the processing unit 158 according to the first example may be provided without the distance calculating unit 162. In this case, the display control unit 164 causes an annotation image to be displayed on the display screen, the annotation image corresponding to information indicating a distance acquired from the external device.

Furthermore, the processing unit 158 according to the first example may have a configuration according to a way in which the processing related to the display control method according to the embodiment is divided.

[2-2-2] Second Example of Processing According to Display Control Method

Figure 11:
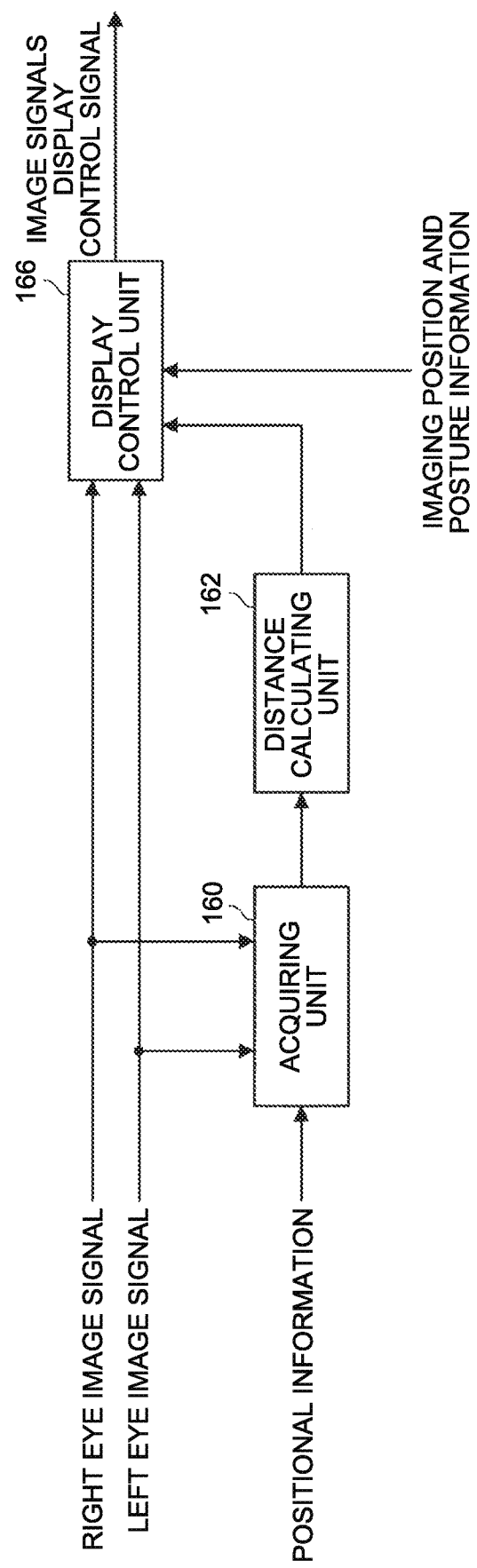
FIG. 11 is a functional block diagram illustrating a second example of the configuration of the processing unit included in the medical observation apparatus according to the embodiment.

FIG. 11 is a functional block diagram illustrating a second example of a configuration of the processing unit 158 included in the medical observation apparatus 100 according to the embodiment.

The processing unit 158 has, for example, the acquiring unit 160, the distance calculating unit 162, and a display control unit 166. The processing unit 158 according to the second example illustrated in FIG. 11 basically has the same functions as the processing unit 158 according to the first example illustrated in FIG. 8, but functions that the display control unit 166 has are different from the functions that the display control unit 164 illustrated in FIG. 8 has. Parts of a functional configuration of the processing unit 158 according to the second example will be described below, the parts being different from those of the processing unit 158 according to the first example illustrated in FIG. 8, and description of the same parts will be omitted.

Similarly to the display control unit 164 illustrated in FIG. 8, the display control unit 166 causes a captured right eye medical image, a captured left eye medical image, and an annotation image, to be displayed on the display screen of the display device 200.

Furthermore, the display control unit 166 changes the display of the annotation image correspondingly to any change in one or both of position and posture of the imaging unit 150.

A change in one or both of the position and posture of the imaging unit 150 corresponds to a change in one or both of position and posture of the imaging device 106 that functions as the imaging unit 150. A change in the position and a change in the posture of the imaging device 106 are detected by, for example, angle sensors (not illustrated in the drawings) respectively provided in the above described joints 110*a*, 110*b*, 110*c*, 110*d*, 110*e*, and 110*f*. A change in the position and a change in the posture of the imaging device 106 may be detected by any method that enables these changes to be detected. In FIG. 11, data representing a change in the position and a change in the posture of the imaging device 106 are illustrated as "imaging position and posture information".

If one or both of the position and posture of the imaging unit 150 is/are changed, the captured right eye medical image and the captured left eye medical image are changed. On the contrary, even if one or both of the position and posture of the imaging unit 150 is/are changed, positions of two points in an observation target acquired based on predetermined operation on the observation target are not changed. Therefore, the distance between the two points acquired based on the predetermined operation on the observation target is not changed even if one or both of the position and posture of the imaging unit 150 is/are changed.

"Realization of display of an annotation image with a captured medical image that has been changed" is enabled by: the predetermined operation being performed on the observation target again; and the above described processing related to the first example being performed by the medical observation apparatus 100 again. However, if a medical worker, such as a surgical operator, needs to perform the predetermined operation on the observation target every time one or both of the position and posture of the imaging unit 150 is changed, the medical worker may feel that this process is burdensome.

The display control unit 166 thus moves the positions of two points on the display screen (hereinafter, referred to as the "display positions of two points", distinctively from the positions of two points in the observation target) correspondingly to the change in one or both of the position and posture of the imaging unit 150. The display positions of two points after this movement may be found by, for example, "calculation by use of the display positions of two points before the movement and an affine matrix corresponding to the change in one or both of the position and posture of the imaging unit 150". The method of determining the display positions of two points after the movement is not particularly limited. The display control unit 166 then causes an annotation image to be displayed, the annotation image corresponding to the display positions of two points after the movement. The annotation image corresponding to the display positions of two points after the movement may be, for example, "an image resulting from rotation, enlargement or reduction, parallel translation, or any combination thereof, of the annotation image before the movement, in a three-dimensional space". For example, the display control unit 166 reads an annotation image corresponding to information indicating a distance and display positions of two points, from a recording medium (not illustrated in the drawings), and causes the read annotation image to be displayed on the display screen of the display device 200. In a specific example, the recording medium (not illustrated in the drawings) has, stored therein beforehand, for example, "an image resulting from rotation, enlargement or reduction, parallel translation, or any combination thereof, of an annotation image, in a three-dimensional space", for each combination of display positions of two points before movement and display positions of two points after the movement". The display control unit 166 reads an image corresponding to a combination of display positions of two points before movement and display positions of two points after the movement as the annotation image corresponding to the display positions of two points after the movement, from the recording medium (not illustrated in the drawings), and causes the read annotation image to be displayed on the display screen of the display device 200. The annotation image corresponding to the display positions of two points after the movement is not limited to the example described above. For example, the display control unit 166 may perform affine transformation on a reference image that is an annotation image read from a recording medium similarly to the processing related to the display control method according to the first example, and thereby generate an annotation image corresponding to display positions of two points after movement.

The processing unit 158 that performs the processing related to the display control method according to the second examples basically has the same configuration as the processing unit 158 according to the first example illustrated in FIG. 8. Therefore, similarly to the processing unit 158 according to the first example illustrated in FIG. 8, the processing unit 158 according to the second example is able to cause an annotation image as represented by "C" in FIG. 6 or illustrated in FIG. 7, to be displayed together with a captured medical image.

Furthermore, the processing unit 158 according to the second example automatically changes display of an annotation image correspondingly to any change in one or both of position and posture of the imaging unit 150. That is, a medical worker who uses the medical observation apparatus 100 that performs the processing related to the display control method according to the second example does not need to perform predetermined operation on an observation target every time one or both of the position and posture of the imaging unit 150 is changed.

Therefore, the medical observation apparatus 100 that performs the processing related to the display control method according to the second example enables improvement in the convenience for a user of the medical observation apparatus 100, more than the medical observation apparatus 100 that performs the processing related to the display control method according to the first example.

The functional configuration of the processing unit 158 according to the second example is not limited to the example illustrated in FIG. 11.

For example, in the processing unit 158 according to the second example, the display control unit 166 may have a function of the distance calculating unit 162.

Furthermore, if the processing in the distance calculating unit 162 is performed in a device external to the medical observation apparatus 100, the processing unit 158 according to the second example may be provided without the distance calculating unit 162. In this case, the display control unit 166 causes an annotation image to be displayed on the display screen, the annotation image corresponding to information indicating a distance acquired from the external device.

Furthermore, the processing unit 158 according to the second example may have a configuration according to a way in which the processing related to the display control method according to the embodiment is divided.

[2-2-3] Third Example of Processing Related to Display Control Method

Figure 12:
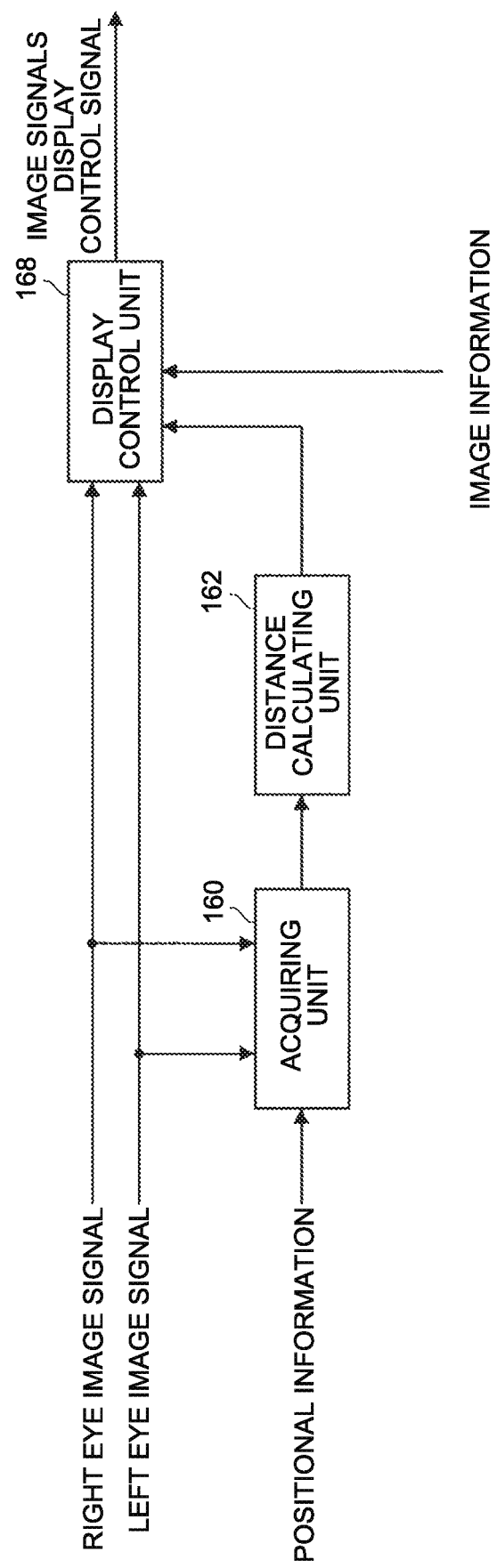
FIG. 12 is a functional block diagram illustrating a third example of the configuration of the processing unit included in the medical observation apparatus according to the embodiment.

FIG. 12 is a functional block diagram illustrating a third example of the configuration of the processing unit 158 included in the medical observation apparatus 100 according to the embodiment.

The processing unit 158 has, for example, the acquiring unit 160, the distance calculating unit 162, and a display control unit 168. The processing unit 158 according to the third example illustrated in FIG. 12 basically has the same functions as the processing unit 158 according to the first example illustrated in FIG. 8, but functions that the display control unit 168 has are different from the functions that the display control unit 164 illustrated in FIG. 8 has. Parts of a functional configuration of the processing unit 158 according to the third example will be described below, the parts being different from those of the processing unit 158 according to the first example illustrated in FIG. 8, and description of the same parts will be omitted.

Similarly to the display control unit 164 illustrated in FIG. 8, the display control unit 168 causes a captured right eye medical image, a captured left eye medical image, and an annotation image, to be displayed on the display screen of the display device 200.

Furthermore, the display control unit 168 causes an image to be displayed on the display screen, the image representing a medical tool corresponding to a distance between two points. For example, the display control unit 168 causes an image to be displayed on one or both of the display screen of the display device 200 where the captured right eye medical image and captured left eye medical image are displayed and a display screen of another display device, the image representing a medical tool.

Examples of the image representing a medical tool corresponding to a distance between two points include an image of a clip corresponding to a distance between two points, as described already as another example of the annotation image. The image representing a medical tool corresponding to a distance between two points is not limited to an image of clip, and may be an image of any medical tool corresponding to an operative surgical procedure, such as a surgical needle or a surgical suture.

For example, the display control unit 168 reads an image representing a medical tool corresponding to a distance between two points, from a recording medium (not illustrated in the drawings) that functions as a storage unit (not illustrated in the drawings), and causes the read image to be displayed on the display screen of the display device 200. Data representing an image representing a medical tool corresponding to a distance between two points are illustrated as "image information" in FIG. 12.

Figure 13:
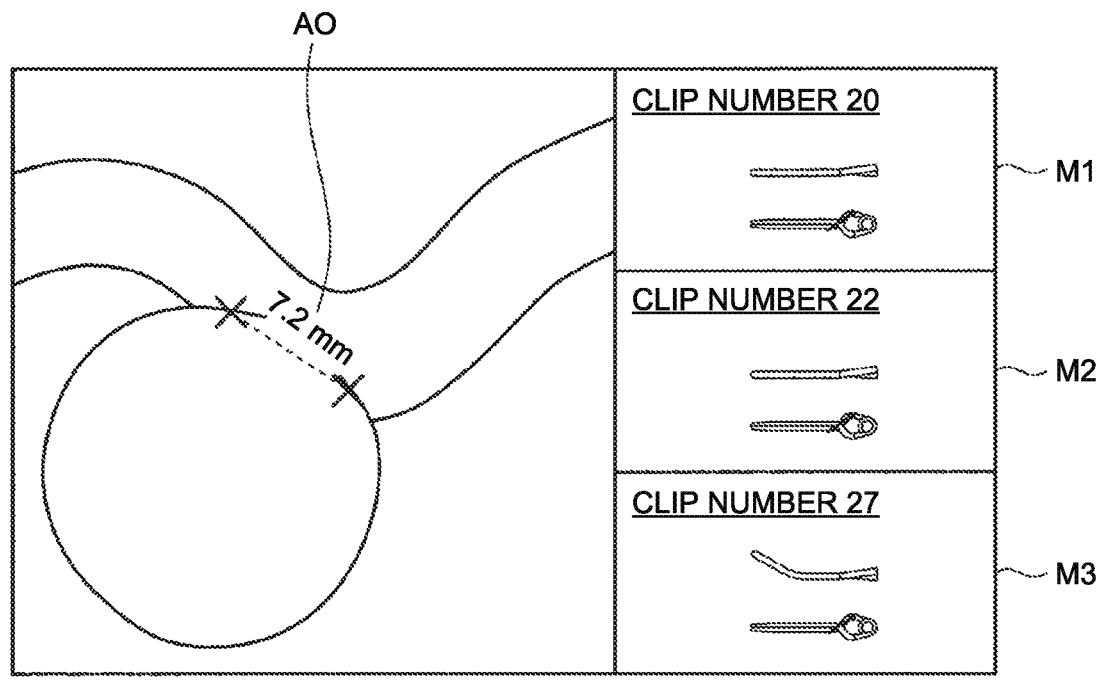
FIG. 13 is an explanatory diagram for explanation of an example of an image displayed by the display control method according to the embodiment.

FIG. 13 is an explanatory diagram for explanation of an example of an image displayed by the display control method according to the embodiment. FIG. 13 illustrates "an example where images M1, M2, and M3 (examples of images representing medical tools, the same applying hereinafter) of clips corresponding to a distance between two points are being displayed further, in addition to a captured medical image having the annotation image represented by "C" in FIG. 6 superimposed thereon".

For example, as illustrated in FIG. 13, by the display of the images M1, M2, and M3 of the clips corresponding to the distance between two points, a surgical operator is able to select a clip easily. Furthermore, easy selection of a clip leads to reduction of the burden on the surgical operator and reduction in the time of maneuvers.

The image displayed by the display control method according to the third example is not limited to the example illustrated in FIG. 13. For example, an image of a clip corresponding to a distance between two points may be displayed at the position of the annotation image AO illustrated in FIG. 13. That is, an image representing a medical tool may be displayed superimposed on one or both of a captured right eye medical image and a captured left eye medical image.

The processing unit 158 that performs processing related to the display control method according to the third example basically has the same configuration as the processing unit 158 according to the first example illustrated in FIG. 8. Therefore, similarly to the processing unit 158 according to the first example illustrated in FIG. 8, the processing unit 158 according to the third example is able to cause an annotation image as represented by "C" in FIG. 6 or illustrated in FIG. 7, to be displayed, together with a captured medical image.

Furthermore, the processing unit 158 according to the third example causes an image to be displayed on the display screen, the image representing a medical tool corresponding to a distance between two points. A medical worker, such as a surgical operator, is able to select a medical tool corresponding to a distance between two points easily.

Therefore, the medical observation apparatus 100 that performs the processing related to the display control method according to the third example enables improvement of the convenience for a user of the medical observation apparatus 100, more than the medical observation apparatus 100 that performs the processing related to the display control method according to the first example.

The functional configuration of the processing unit 158 according to the third example is not limited to the example illustrated in FIG. 12.

For example, in the processing unit 158 according to the third example, the display control unit 168 may have a function of the distance calculating unit 162.

Furthermore, if the processing in the distance calculating unit 162 is performed in a device external to the medical observation apparatus 100, the processing unit 158 according to the third example may be provided without the distance calculating unit 162. In this case, the display control unit 168 causes an annotation image to be displayed on the display screen, the annotation image corresponding to information indicating a distance acquired from the external device.

Furthermore, the processing unit 158 according to the third example may have a configuration according to a way in which the processing related to the display control method according to the embodiment is divided.

[2-2-4] Another Example of Processing Related to Display Control Method

The processing related to the display control method according to the embodiment is not limited to the above described first to third examples. For example, the processing unit 158 included in the medical observation apparatus 100 according to the embodiment may perform processing that is a combination of the processing according to the second example and the processing according to the third example.

[3] Example of Effects Achieved by Use of Display Control Method According to Embodiment By use of the display control method according to the embodiment, for example, the following effects are achieved. Needless to say, effects achieved by use of the display control method according to the embodiment are not limited to the following examples.

A medical worker, such as a surgical operator, is able to perceive a result of measurement of a distance between two points in the field of view for observation in a captured medical image in real time, and thus use of an additional tool for measurement, such as a measuring tape, is not needed and improvement in efficiency of the surgical operation is able to be expected.

By the result of measurement of the distance between two points in the field of view for observation being able to be perceived in real time in the captured medical image, accuracy of selection of a medical tool, such as a clip, is improved, and reduction of risk of complications or injury is able to be expected, together with the improvement in the efficiency of the surgical operation.

Program According to Embodiment

Convenience for a user of the medical observation apparatus according to the embodiment is able to be improved by execution of a program (for example, a program that enables execution of the processing related to the display control method according to the embodiment) by a processor or the like in a computer system, the program being for causing the computer system to function as the medical observation apparatus. The computer system according to the embodiment may be a single computer, or plural computers. The processing related to the display control method according to the embodiment is executed by the computer system according to the embodiment.

The above described effects achieved by the display realized by the processing related to the display control method according to the embodiment are able to be achieved by execution of the program by the processor or the like in the computer system, the program being for causing the computer system to function as the medical observation apparatus according to the embodiment.

Preferred embodiments of the present disclosure have been described thus far in detail by reference to the appended drawings, but the technical scope of the present disclosure is not limited to these examples. It is evident that any person having ordinary knowledge in the technical field of the disclosure is able to devise various modified examples and reformed examples within the scope of technical ideas described in the claims, and these examples will of course be understood as belonging to the technical scope of the disclosure.

For example, according to the above description, the program (a computer program) for causing the computer system to function as the medical observation apparatus according to the embodiment is provided, but according to the embodiment, a recording medium storing therein the program may also be provided.

The above described configurations are examples of the embodiment, and of course belong to the technical scope of the disclosure.

Furthermore, the effects described in the specification are just explanatory or exemplary, and are not limiting. That is, the techniques according to the disclosure may achieve, together with the above described effects, or instead of the above described effects, any other effect evident to those skilled in the art from the description in the specification.

The following configurations also belong to the technical scope of the disclosure.

(1) A medical observation apparatus, comprising:
an imaging device configured to capture an observation target to obtain a captured right eye medical image and a captured left eye medical image;
circuitry configured to:
acquire positions of at least two points in the observation target, the positions being determined based on predetermined operation on the observation target; and
cause the captured right eye medical image, the captured left eye medical image, and an annotation image, to be displayed on a display screen of a display device, the annotation image indicating a distance between two points at the acquired positions.

(2) The medical observation apparatus according to (1), wherein the circuitry is configured to cause the annotation image to be displayed superimposed on one or both of the captured right eye medical image and the captured left eye medical image.

(3) The medical observation apparatus according to (1) or (2), wherein when plural pairs of the positions of two points have been acquired, the circuitry causes the annotation images to be displayed on the display screen, the annotation images corresponding respectively to the distances between two points.

(4) The medical observation apparatus according to any one of (1) to (3), wherein the circuitry is configured to acquire the positions by detecting an object corresponding to the predetermined operation, from one or both of the captured right eye medical image and the captured left eye medical image.

(5) The medical observation apparatus according to any one of (1) to (3), wherein the circuitry is configured to acquire the positions by acquiring positional information indicating the positions, from a detecting device that detects the positions.

(6) The medical observation apparatus according to any one of (1) to (5), wherein the circuitry is further configured to change the display of the annotation image correspondingly to a change in one or both of position and posture of the imaging device.

(7) The medical observation apparatus according to any one of (1) to (6), wherein the circuitry is further configured to cause an image to be displayed on the display screen of the display device or a display screen of another display device, the image representing a medical tool corresponding to the distance between two points.

(8) The medical observation apparatus according to any one of (1) to (7), wherein the circuitry is further configured to calculate the distance between two points, and
the circuitry causes the annotation image to be displayed, the annotation image indicating the calculated distance.

(9) The medical observation apparatus according to any one of (1) to (8), further comprising:
an arm formed of plural links connected to one another via joints, wherein
the imaging device is supported by the arm.

(10) The medical observation apparatus according to any one of (1) to (8), wherein the imaging device is inserted into a body of a patient, and capture an image of the interior of the body, the interior being the observation target.

According to the disclosure, convenience for a user of a medical observation apparatus is able to be improved.

The above effect is not necessarily limiting; and in addition to the above effect, or instead of the above effect, any effect described in this specification or any other effect perceivable from the specification may be achieved.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation system, comprising: an imaging device configured to capture an observation target to obtain a right eye medical image and a left eye medical image; and circuitry configured to: acquire positions of at least two points in the observation target, the positions being determined based on predetermined operation on the observation target, the acquired positions defining a lesion in the observation target; cause the right eye medical image, the left eye medical image, and an annotation image, to be displayed on a display screen of a display device, the annotation image indicating a distance between two points at the acquired positions, the distance being a length of at least a part of the lesion, wherein the annotation image includes a numerical value corresponding to the distance between two points at the acquired positions; and cause an image to be displayed on the display screen of the display device or a display screen of another display device, the image representing a medical tool be used based on the distance between two points, wherein the image representing the medical tool is displayed separately from the right eye medical image, the left eye medical image, and the annotation image, and the image representing the medical tool includes at least two medical tools be used based on the distance between two points displayed separately from the right eye medical image, the left eye medical image, and the annotation image and each other.

2. The medical observation system according to claim 1, wherein the circuitry is further configured to cause the annotation image to be displayed superimposed on one or both of the right eye medical image and the left eye medical image.

3. The medical observation system according to claim 1, wherein when in a case where plural pairs of the positions of two points are acquired, the circuitry causes the annotation images to be displayed on the display screen, the annotation images corresponding respectively to the distances between two points.

4. The medical observation system according to claim 1, wherein the circuitry is further configured to acquire the positions by detecting an object corresponding to the predetermined operation, from one or both of the right eye medical image and the left eye medical image.

5. The medical observation system according to claim 1, wherein the circuitry is configured to acquire the positions by acquiring positional information indicating the positions, from a detecting device that detects the positions.

6. The medical observation system according to claim 1, wherein the circuitry is further configured to change the display of the annotation image correspondingly to a change in one or both of position and posture of the imaging device.

7. The medical observation system according to claim 1, wherein the circuitry is further configured to calculate the distance between two points, and
the circuitry causes the annotation image to be displayed, the annotation image indicating the calculated distance.

8. The medical observation system according to claim 1, further comprising:
an arm formed of plural links connected to one another via joints, wherein
the imaging device is supported by the arm.

9. The medical observation system according to claim 1, wherein the imaging device is inserted into a body of a patient, and captures an image of the interior of the body, the interior being the observation target.

10. The medical observation system according to claim 1, wherein the circuitry is further configured to display images of tools to be used based on the distance between two points at the acquired positions.

11. The medical observation system according to claim 1, wherein the acquired positions are not spaced from one another by a predetermined amount.

12. The medical observation system according to claim 1, wherein the circuitry is further configured to calculate the distance between two points at the acquired positions.

13. The medical observation system according to claim 1, wherein the length of the lesion is a length of the lesion in a field of view of the observation target.

14. The medical observation system according to claim 1, wherein the image representing the medical tool includes at least one of an image of the medical tool, a model number of the medical tool or an image indicating a name of the medical tool.

15. A medical display system, comprising: circuitry configured to: acquire positions of at least two points in an observation target imaged by a sensor that obtains a right eye medical image and a left eye medical image of the observation target, the positions being determined based on predetermined operation on the observation target, the acquired positions defining a lesion in the observation target; and cause the right eye medical image, the left eye medical image, and an annotation image, to be displayed on a display screen of a display, the annotation image indicating a distance between two points at the acquired positions, the distance being a length of at least a part of the lesion; and cause an image to be displayed on the display screen of the display or a display screen of another display, the image representing a medical tool to be used based on the distance between two points, wherein the annotation image includes a numerical value corresponding to the distance between two points at the acquired positions, the image representing the medical tool is displayed separately from the right eye medical image, the left eye medical image, and the annotation image, and the image representing the medical tool includes at least two medical tools be used based on the distance between two points displayed separately from the right eye medical image, the left eye medical image, and the annotation image and each other.

16. A medical display method, comprising: acquiring positions of at least two points in an observation target imaged by a sensor that obtains a right eye medical image and a left eye medical image of the observation target, the positions being determined based on predetermined operation on the observation target, the acquired positions defining a lesion in the observation target; and displaying the right eye medical image, the left eye medical image, and an annotation image, a display screen of a display, the annotation image indicating a distance between two points at the acquired positions, the distance being a length of at least a part of the lesion, wherein the annotation image includes a numerical value corresponding to the distance between two points at the acquired positions; and displaying, on the display screen of the display or a display screen of another display, an image representing a medical tool to be used based on the distance between two points, wherein the image representing the medical tool is displayed separately from the right eye medical image, the left eye medical image, and the annotation image, and the image representing the medical tool includes at least two medical tools be used based on the distance between two points displayed separately from the right eye medical image, the left eye medical image, and the annotation image and each other.

17. The medical display method according to claim 16, wherein the image representing the medical tool includes at least one of an image of the medical tool, a model number of the medical tool or an image indicating a name of the medical tool.

18. The medical display system according to claim 15, wherein the image representing the medical tool includes at least one of an image of the medical tool, a model number of the medical tool or an image indicating a name of the medical tool.

* * * * *